United States Patent [19]

Baker et al.

[11] Patent Number: 5,721,257
[45] Date of Patent: *Feb. 24, 1998

[54] METHOD AND THERAPEUTIC SYSTEM FOR SMOKING CESSATION

[75] Inventors: Richard W. Baker, Palo Alto, Calif.; Giancarlo Santus, Milan, Italy; Susan Vintilla-Friedman, Cupertino, Calif.

[73] Assignee: Pharmacia & Upjohn AB, Sweden

[*] Notice: The term of this patent shall not extend beyond the expiration date of Pat. No. 5,362,496.

[21] Appl. No.: 484,987

[22] Filed: Jun. 7, 1995

Related U.S. Application Data

[63] Continuation of Ser. No. 221,914, Mar. 31, 1994, Pat. No. 5,593,684, which is a continuation of Ser. No. 103,262, Aug. 4, 1993, Pat. No. 5,362,496.

[51] Int. Cl.$^6$ ............................ A61K 31/44; A61K 9/70
[52] U.S. Cl. ........................... 514/343; 514/813; 424/449
[58] Field of Search ................................. 514/343, 813; 424/449

[56] References Cited

U.S. PATENT DOCUMENTS

| | | | |
|---|---|---|---|
| 4,839,174 | 6/1989 | Baker | 424/447 |
| 4,943,435 | 7/1990 | Baker | 424/448 |
| 5,135,753 | 8/1992 | Baker | 424/435 |
| 5,362,496 | 11/1994 | Baker | 424/435 |

FOREIGN PATENT DOCUMENTS

| | | |
|---|---|---|
| 41057/89 | 9/1989 | Australia. |
| 610299 | 9/1989 | Canada. |
| 4341/89 | 9/1989 | Denmark. |
| 89308978 | 9/1989 | European Pat. Off.. |
| 1-253690 | 9/1989 | Japan. |
| 17462 | 9/1989 | Mexico. |
| 230554 | 9/1989 | New Zealand. |
| 89.3570 | 9/1989 | Norway. |

*Primary Examiner*—Theodore J. Criares
*Attorney, Agent, or Firm*—Pravel, Hewitt, Kimball & Krieger

[57] ABSTRACT

A method for treating conditions responsive to nicotine therapy, and particularly for smoking cessation therapy and for reducing nicotine craving, is described that utilizes transdermal nicotine delivery for obtaining base-line nicotine plasma levels coupled with transmucosal administration of nicotine to satisfy transient craving.

5 Claims, 12 Drawing Sheets

METHOD AND THERAPEUTIC SYSTEM FOR SMOKING CESSATION

This is a continuation of application Ser. No. 08/221,914 filed Mar. 31, 1994, now U.S. Pat. No. 5,593,684, which is a continuation of Ser. No. 08/103,262, filed Aug. 4, 1993, now U.S. Pat. No. 5,362,496.

BACKGROUND OF THE INVENTION

This invention pertains to methods and therapeutic systems for treating a condition responsive to nicotine therapy, and particularly for smoking cessation. More specifically, this invention is directed to methods comprising the transdermal administration of nicotine, in combination with the transmucosal administration of nicotine to provide additional periodic doses of nicotine.

Nicotine replacement therapy as an aid to quitting smoking has been become increasingly popular. Nicotine chewing gum (nicotine polacrilex) and transdermal nicotine are two of the more popular forms of nicotine replacement available commercially. It has become clear, however, that the mere replacement of cigarettes with another nicotine source may not be sufficient to insure success in smoking cessation therapy. Specifically, conventional nicotine replacement therapy does not adequately address the symptoms associated with the cessation of smoking.

Of the many smoking withdrawal symptoms, craving for cigarettes is one of the most difficult to alleviate. As described in Steuer, J. D. and Wewers, M. E. in *Oncology Nursing Forum* 1989, 16, 193–198, cigarette craving is one of the most consistent, most severe, and earliest withdrawal symptoms experienced by those attempting to quit smoking. Some reports suggest that craving peaks over the first 24 to 72 hours of abstinence and then declines, although craving has been reported after five years of abstinence.

Research is focusing on the factors that precipitate craving in an attempt to better understand and deal with the problem of relapse. Some investigators believe that certain smokers are much more likely than others to experience craving symptoms, especially when trying to quit smoking. Based on literature reports and his own investigations, Harrington (in *Br. J. Soc. Clin. Psychol.* 1978, 17, 363–371) reported that smokers can be separated by craving versus noncraving status, and that these separate populations have different responses to smoking cessation therapy.

Most commercially available products for nicotine replacement in smoking cessation therapy have not specifically addressed the issue of satisfying craving for nicotine. Instead, as mentioned above, they have generally been targeted towards providing a stable baseline level of nicotine in the blood. Some evidence indicates that low consistent blood levels of nicotine (as provided by transdermal nicotine, and to a lesser extent by nicotine gum) relieve some of the symptoms of nicotine withdrawal, but craving symptoms may not be among these (see Russell, M. A. H. in *Nicotine Replacement: a Critical Evaluation;* Pomerleau, O. F. and Pomerleau, C. S., Eds.; Alan R. Liss, Inc.: New York, 1988; pp 63–94). This may be because cigarette smoking provides an initial sharp rise in blood level, which is missing in these nicotine replacement therapies. The blood level peak produced by cigarettes is both higher (between 30–40 ng/mL) and sharper (this peak is attained within 10 minutes) than the steadier levels obtained from polacrilex gum or a transdermal system. Russell states that the optimal steady-state blood level for nicotine replacement is between 10–15 ng/mL, but that quick-rise effects are probably necessary for more complete relief from craving in the early stages of cigarette withdrawal. His investigations suggested that a rise in nicotine blood level of at least 10 ng/mL in 10 minutes is required to obtain postsynaptic effects at nicotinic cholinergic receptors in the central nervous system and at autonomic ganglia. These postsynaptic effects may be responsible for the feelings such as lightheadedness or dizziness experienced by cigarette smokers. See, also, Benowitz and Jacob (1984) *Clin. Pharmacol. Ther.* 36:265–270.

As mentioned above, nicotine gum (nicotine. polacrilex) is one of the commercially available sources of nicotine for replacement therapy. This particular nicotine gum is actually an ion-exchange resin that releases nicotine slowly when the patient chews, and the nicotine present in the mouth is delivered directly to the systemic circulation by buccal absorption. However, much of the nicotine is retained in the gum through incomplete chewing or is largely wasted through swallowing, so that the systemic bioavailability of nicotine from this gum is low and averages only 30–40%. Moreover, compared with cigarette smoking, this form of nicotine gum is a slow and inefficient source of nicotine. In addition, during ad libitum clinical or experimental use, the 2-mg gum produces steady-state blood nicotine levels that average around one third of the blood level peaks obtained from cigarette smoking. Thus, nicotine gum, when used alone, is frequently not effective as a method for smoking cessation.

Nicotine replacement through transdermal nicotine systems is another therapy that has become commercially available. These nicotine patches provide a low, consistent blood level of nicotine to the user, and bypass the first pass effects of the gut and liver. The concept of applying the teachings of transdermal drug therapy to the delivery of nicotine has been described in the literature, and particularly in U.S. Pat. Nos. 4,839,174, 5,135,753, and U.S. Pat. No. 4,943,435, herein incorporated by reference.

Nicotine is a suitable candidate for transdermal therapy because it is volatile, highly lipid soluble, and permeates the skin easily. It is, however, a reactive liquid and a strong solvent. Therefore, transdermal nicotine systems must be made of materials that are compatible with nicotine and can release nicotine at a safe, useful flux. In addition, these systems should be designed to exploit the benefits of controlled release transdermal therapy. In general, one of the recognized advantages of transdermal therapy as opposed to other drug administration techniques is the simplicity of the dosing regime. Another major advantage of continuous transdermal delivery is that the blood plasma levels of the delivered agent remain relatively steady. In this way, the periodic fluctuations between plasma levels above the safe threshold and below the efficacy threshold that are often seen with oral tablets or injections are eliminated, as are the "highs" associated with addictive substances.

The primary use of transdermal nicotine systems to date has been for smoking cessation therapy. A study by Rose, J. E. et al. (1985) *Clin. Pharmacol. Ther.* 38:450–456 demonstrated that systemic delivery of nicotine in pharmacologically useful amounts was feasible by the transdermal route. Studies using human cadaver skin in vitro are likewise consistent with this finding. Typical permeabilities during the first day of patch use are on the order of 0.1 mg/cm$^2$·h, increasing to 0.4 mg/cm$^2$·h and more at later times. Systemic absorption of 20 mg of nicotine (approximately equivalent to smoking one pack of cigarettes) per day would then be theoretically achievable with a dermal administration area of about 10 cm$^2$. This surface area is well within the range of appropriate sizes for transdermal delivery systems.

In addition, human clinical studies by Dubois et al. (1989) *Meth. and Find. Exp. Clin. Pharmacol.* 11:187–195, for example, have demonstrated that application of transdermal nicotine systems results in nicotine blood levels on the order of 10–20 ng/mL, which is comparable to the minimum nicotine blood levels of moderately heavy cigarette smokers. Application of patches for 16 to 24 hours resulted in relatively constant blood levels in this range, indicating that the systems are useful for reliable long-term delivery of nicotine.

Several groups of investigators have described clinical studies that investigated efficacy and safety of transdermal nicotine systems for smoking cessation. Abelin et al. (1989) *The Lancet* 1:7–10 reported on the results of a double-blind study in which they determined that long-term use of a transdermal nicotine patch significantly increased the quit rate in cigarette smokers. The results of this study showed that the number of abstainers in the transdermal nicotine group after one, two, and three months of treatment was significantly greater compared to the placebo group. In another study reported by Mulligan et al. (1990) *Clin. Pharmacol. Ther.* 47:331–337, the use of a transdermal nicotine patch in a 6-week placebo-controlled double-blind study resulted in a significant degree of smoking cessation. Finally, a report by Rose et al. (1990) *Clin. Pharmacol. Ther.* 47:323–330 of a randomized double-blind trial indicates that certain smoking withdrawal symptoms were relieved by use of a transdermal nicotine system.

Therefore, transdermal nicotine systems can be designed to provide higher steady-state blood levels of nicotine, but are unable to provide blood level peaks or to provide a rapid increase in blood level. Thus, both nicotine gum and transdermal nicotine compete with each other as products providing steady-state nicotine blood levels, but do not satisfy craving symptoms for cigarettes in some smokers.

Other nicotine replacement products that are on the market or have been proposed in the literature have not been of serious interest in smoking cessation therapy, because of problems related to their use, and also because of limited ability to satisfy craving for cigarettes. Nicotine vapor has been delivered to patients in aerosol form, similar to the inhaler technology used to supply bronchial asthma medications, and in a "smokeless cigarette" such as that marketed by Advanced Tobacco Products under the trade name Favor®.

Another smokeless version of nicotine delivered to the buccal mucosa is provided by chewing tobacco, oral snuff, or tobacco sachets. Tobacco sachets, which are especially popular in Scandinavia and the U.S., contain ground tobacco in packets that are sucked or held in the mouth.

The literature describes other capsules, tablets, and lozenges for oral delivery of nicotine. For example, WO 803803 discloses a chewable capsule filled with a liquid containing 0.1–10.0 mg of nicotine, together with additives for improving flavor and dispersion. The capsules are provided in a variety of pH values to allow the patient a choice of nicotine absorption rate, and are especially intended as an aid to quitting smoking.

Another nicotine capsule formulation is disclosed by M. E. Jarvik et al. (1970) *Clin. Pharm. Ther.* 11:574–576 for ingestion as a smoking cessation aid. These capsules, however, were apparently swallowed whole by the subjects, according to the theory that intestinal absorption of nicotine could produce significant blood levels. The study showed a small but significant decrease in the number of cigarettes smoked by subjects, but no quantitative measurements of nicotine blood levels were obtained.

The literature also describes different designs of tablets for delivering nicotine to the mouth and digestive system. BE 899037 discloses a tablet containing 0.1 to 5 mg nicotine as a base or water-soluble acid salt as an aid for quitting smoking.

Wesnes and Warburton (1984) *Psychopharmacology* 82:147–150; and (1986) *Psychopharmacology* 89:55–59 discuss the use of nicotine tablets in experiments examining the effects of nicotine on learning and information processing. In the first experiment, nicotine was added to dextrose tablets with a drop of tabasco sauce added to disguise the taste of nicotine. In the second experiment, nicotine was added to magnesium hydroxide tablets, under the theory that an alkaline environment in the mouth would enhance buccal absorption. Again, tabasco sauce was added to the tablets to mask the taste of nicotine in both active and placebo tablets. The subjects were instructed to hold the tablets in the mouth for minutes before swallowing, in order to maximize contact with the buccal mucosa.

Shaw (for example in GB 2142822 and U.S. Pat. No. 4,806,356) describes a nicotine lozenge prepared from a mixture of inert filler material, a binder, and either pure nicotine or a nicotine-containing substance by cold compression. WO 9109599 describes a nicotine product for oral delivery in the form of an inclusion complex of nicotine and a cyclodextrin compound. The patent also discusses the use of various excipients and direct compression for manufacture of the product.

In recent years, several nicotine lozenges have been commercialized and are available as over-the-counter products in the U.K. Resolution® lozenges, manufactured by Phoenix Pharmaceuticals and distributed by Ernest Jackson, contain 0.5 mg nicotine, together with the anti-oxidant vitamins A, C, and E. Stoppers® lozenges, distributed by Charwell pharmaceuticals Ltd., contain 0.5 mg nicotine and are available in chocolate, orange and peppermint flavors.

To date, it has been difficult to deliver nicotine in a profile mimicking the nicotine blood levels achieved by consistent smoking, to satisfy cravings for nicotine in people who are attempting to quit smoking, and thus, to provide greater protection against relapse than other nicotine replacement therapies for people who are trying to quit smoking. It is therefore desirable to provide improved compositions and methods which avoid the disadvantages of these conventional nicotine delivery devices and methods while providing an effective means for delivering nicotine for smoking cessation treatment, for reducing nicotine craving, and for treating other conditions responsive to nicotine therapy.

SUMMARY OF THE INVENTION

The present invention consists of a method for treating a condition responsive to nicotine therapy, and particularly for smoking cessation therapy and for reducing nicotine craving, comprising the steps of:

i) a first treatment with nicotine by transdermal administration to obtain nicotine blood levels of between 5 to 35 ng/mL for at least 12 hours; and ii) a second treatment with nicotine by transmucosal administration to obtain maximum nicotine blood levels from 2 to 20 minutes after the transmucosal administration; and wherein the transmucosal administration provides transient blood levels of nicotine about 5 ng/ml above that provided by the transdermal administration of nicotine.

In a preferred embodiment, the transmucosal administration results in maximum nicotine blood levels from about 2 to 30 minutes, preferably from about 2 to 20 minutes, and more preferably from about 2 to 10 minutes, after the transmucosal administration of nicotine and is obtained by allowing a nicotine lozenge to completely dissolve in the mouth. According to a particularly preferred embodiment, the nicotine lozenge will comprise nicotine, an absorbent excipient, such as mannitol or β-cyclodextrin, and a nonnutritive sweetener, such as xylitol, optionally in combination with ammonium glycyrrhizinate.

According to other embodiments, the transmucosal administration of nicotine is obtained through the use of a nicotine containing gum, nicotine sublingual tablets or capsules.

The transdermal administration of nicotine is preferably obtained by administering a transdermal system comprising:

(a) a nicotine depot layer, having a skin-facing side and a skin-distal side, the depot layer containing a sufficient quantity of nicotine to maintain a useful flux of nicotine from the patch for a total time period of 12 hours or more;

(b) an occlusive backing layer in contact with and covering the depot layer on the skin-distal side; and (c) rate-controlling means for controlling diffusion of nicotine from the skin-facing side at a first flux of greater than zero but less than 2 mg/cm$^2$ in any hour for a first time period of greater than zero but less than 5 hours, then at a second flux between 20 and 800 mu g/cm$^2$·h for a second time period of 7 hours or more.

According to other embodiments, the patch may take the form of a reservoir system, in which the depot of nicotine is separated from the skin by a nonporous polymeric membrane, through which the nicotine diffuses at a controlled rate. The patch may also be in the form of a monolithic matrix, consisting of a single phase solution or mixture of nicotine in a polymeric material, and wherein the nicotine is released by diffusion through the solution. A third possible embodiment involves a combined system from which nicotine is released by a combination of diffusion through a polymeric solution, and diffusion across a polymeric membrane. Embodiments employing a monolith of nicotine in a polymeric carrier are particularly preferred.

DESCRIPTION OF THE PREFERRED EMBODIMENT

I. Terminology

Figure 1:
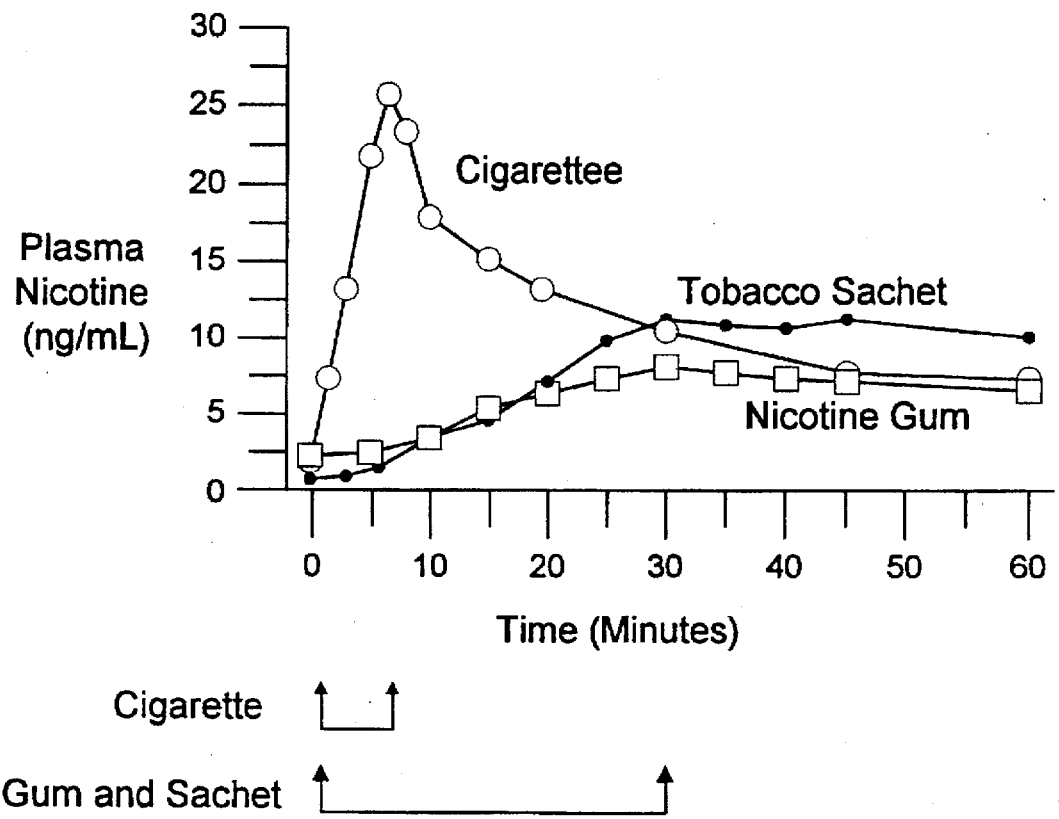
FIG. 1 is a graph of average nicotine plasma levels (nanograms (ng)/milliliter (mL)), resulting from use of cigarettes, tobacco sachets, or nicotine gum, as a function of time (minutes).

Unless otherwise stated, the following terms used in the specification and claims have the meanings given below:

"Transdermal system" means any system or device that is attached to the skin of a patient and is used to deliver a drug through the intact skin and into the patient's body.

"Transmucosal administration" or "transmucosal delivery" means any system or device for the administration of a drug across a patient's mucosal membrane, including the oral mucosa, such as the buccal and sublingual mucosa, and other mucosal membranes, including rectal, nasal, and vaginal. See "Controlled Drug Delivery, Fundamentals and Applications", 2nd Ed., Robinson and Lee, eds., Chapter 1, "Influence of Drug Properties and Routes of Drug Administration on the Design of Sustained and Controlled Release Systems", Li et al., Marcel Dekker Inc.: New York, pp. 3–61 (1987).

"Nicotine" refers to nicotine free base, i.e., a compound having the formula:

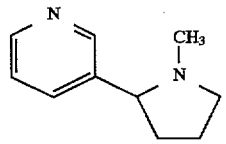

"Nicotine salt" refers to any mono- or bis-pharmaceutically acceptable acid addition salt or metal salt of nicotine.

"Nicotine lozenge" refers to any lozenge, capsule, tablet, or other device for buccal delivery of nicotine.

"Prolonged period" means about 12 hours or more.

"Monolith" means a single-phase combination of nicotine and a polymeric carrier.

"Nonnutritive sweetener" refers to a synthetic or natural substance whose sweetness is higher than or comparable to sucrose and which may have properties such as reduced cariogenicity, health benefits for diabetics, or reduced caloric value compared to sugars.

"Essential oil" refers to a natural oil with a distinctive scent secreted by the glands of certain aromatic plants having terpenes as the major component. Examples of essential oils include, but are not limited to, citrus oils, flower oils (e.g., rose and jasmine), and oil of cloves.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable acid addition salts, see Bundgaard, H., ed., (1985) *Design of Prodrugs*, Elsevier Science Publishers, Amsterdam.

"Pharmaceutically acceptable metal salt" refers to those salts which retain the biological effectiveness and properties of the free bases and which are not biologically or otherwise undesirable, formed with alkali metal ions such as sodium or potassium; alkaline earth metal ions such as calcium and magnesium; and other metal ions such as zinc.

II. Overview

The present invention provides for methods for treating conditions responsive to nicotine therapy, and particularly for smoking cessation therapy and for reducing nicotine craving, comprising the administration of nicotine transdermally and transmucosally. More specifically, the present invention provides for transdermal nicotine systems and systems for the transmucosal administration of nicotine, used together, either sequentially and/or concurrently and in any order, for this purpose, and all methods of use of these systems for this purpose, including but not limited to the embodiments and methods described below.

III. The Transdermal Nicotine System

A. The Monolith System

Figure 2:
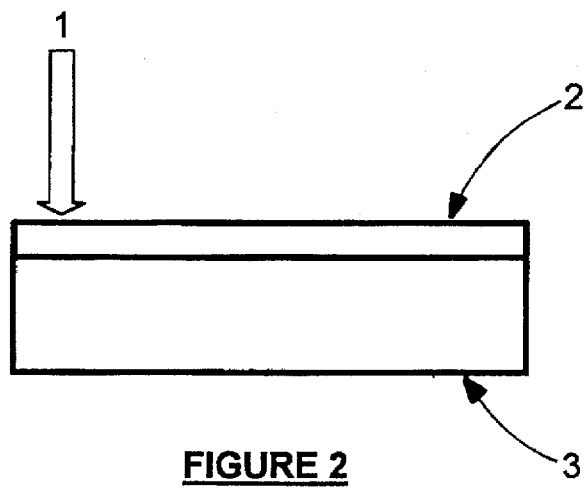
FIG. 2 shows an embodiment of the invention including an impermeable backing (2) and a monolithic nicotine-containing matrix (3).

A basic embodiment of the transdermal nicotine system described in the present invention is shown in FIG. 2. Referring now to this figure, the nicotine dispensing patch, 1, comprises an impermeable backing layer, 2, and a monolithic matrix layer, 3, which both serves as a depot for the nicotine, and controls the rate at which it diffuses to the skin.

1. The Backing Layer

The impermeable backing layer, 2, defines the non-skin facing, or skin distal, side of the patch in use. The functions of the backing layer are to provide an occlusive layer that prevents loss of nicotine to the environment, and to protect the patch. The material chosen should therefore be nicotine resistant, and should exhibit minimal nicotine permeability.

The backing layer should be opaque, because nicotine degrades when exposed to ultraviolet light. Ideally, the backing material should be capable of forming a support onto which the nicotine-containing matrix can be cast, and to which it will bond securely.

A preferred material is polyester or aluminized polyester. Polyester has a nicotine permeability less than 0.2 mu g·100 mu m/cm²·h. Preferred backings are polyester medical films, available for example from 3M Corporation as Scotchpak™ 1005 or 1109. While applicants believe that there are relatively few materials that are really sufficiently impermeable to nicotine to retain the nicotine load adequately during storage or use, other low permeability materials that might be tried include, for example, metal foil, metallized polyfoils, composite foils or films containing polyester, Teflon (polytetrafluoroethylene) type materials, or equivalents thereof that could perform the same function. As an alternative to casting the matrix directly on the backing, the polymer matrix may be cast separately and later adhere to the backing layer.

2. The Monolith Layer

The nicotine monolith layer, 3, comprises nicotine finely dispersed, or preferably dissolved, in a polymer matrix. The monolith layer may be prepared as follows. First a solution of the polymer matrix material is made. Nicotine, preferably liquid, is then added to the polymer solution, and the mixture is homogenized. The percentage by weight of nicotine in the solution may be varied according to the desired loading of the finished monolith. The upper limit on the amount of nicotine that can be incorporated is determined by the stability of the solution. Above about 50 weight percent nicotine, the monolith becomes a solution of the polymer in nicotine, rather than nicotine in the polymer, and depending on the polymer used, a point is reached where it is no longer possible to cast a stable film, because the solution remains in gel form or fluid form after casting.

The monolith solution may be poured into a mold or cast alone or on the desired backing material. The casting is then covered and left for the solvent to evaporate at room temperature. After solvent evaporation, the monolith takes the form of a polymer film typically having a thickness in the range of about 25 to 800 mu m. It will be appreciated that for a given desired total nicotine load, the percentage loading may be varied by varying the monolith thickness. In embodiments where the monolith is formed apart from the backing layer, a backing may be provided, for example, by attaching a layer of single-sided occlusive medical adhesive tape to one face of the cast film.

The total nicotine content of the monolith will be sufficient to provide one day's supply. This amount depends on the user's need for nicotine. [As a rough guide, a delivered load somewhere between 5 mg and 50 mg may be appropriate in smoking cessation therapy.] It is probably not desirable to go above about 50 mg delivered nicotine content, because of the toxicity hazard, although in theory patches of this type with a bigger load can be made. Also, the amount of nicotine in the patch as made may exceed the delivered load because, as the patch becomes exhausted, there will be an insufficient concentration gradient to remove all the nicotine. Consequently, the activity of the patch may fall below useful levels.

A feature of these monolith embodiments is that they provide a solution to the problems of skin irritation and potential toxicity. The activity of nicotine on the skin will be representative of the concentration of nicotine in the monolith. Thus a monolith with a nicotine content of 30 wt % will exhibit the activity of a 30% solution, rather than pure nicotine, on the skin, with consequent substantial reduction or elimination of skin irritation. The release mechanism for the nicotine is diffusion under a concentration gradient. Therefore, even if the patch were to be ingested, the nicotine release would be still a gradual process, and the victim would not be exposed to a very large, toxic, or lethal unit dose. Systems where the nicotine is held in an absorbent material, or mixed in with some other liquid or gel, do not have this advantage.

To ensure that a user cannot be exposed to a toxic dose when the patch is used correctly, the in vitro nicotine flux from the patch must stay within certain limits. This is a much more critical issue with nicotine than with most drugs, because nicotine is very skin permeable, very toxic, and very irritating. The skin flux of nicotine is about 100–300 mu g/cm$^2$·h. However, it should be appreciated that this is a very approximate figure. One of the recognized problems in the art is that skin permeabilities can vary 20-fold or more between individuals and between different skin sites on the same individual. It is thus clear that a patch with a large nicotine load must be able to control release of that load, such that the in vitro flux from the patch does not exceed about 10 times, preferably about 5 times, and more preferably about equals, the average skin permeation rate. Of course, embodiments where the in vitro flux from the patch is less than the skin permeation rate, such that the systemic absorption is controlled primarily by the patch rather than the skin, are acceptable, so long as the systemic nicotine level can be sustained above the necessary minimum level for that individual's needs.

Acrylic adhesives are a preferred polymer for forming monolith films because they can accept a relatively high nicotine loading and still retain good adhesive characteristics. Monsanto's GELVA Multipolymer solution 737 is an example of a particularly preferred acrylic adhesive.

Polyurethanes are also acceptable for forming the monolith films, because they have been found to form stable solutions with nicotine, and they exhibit suitable nicotine permeabilities. The polyurethane used may be a polyether, polycarbonate, hydrocarbon or polyester type. Polyether-type polyurethanes are preferred, because in general they are more inert than polyester-types, and thus more appropriate for biomedical use. Polyether-type polyurethanes are typically made by reacting a dihydroxy-terminated polyether oligomer (diol) with a diisocyanate according to the reaction:

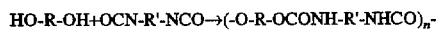

where R is an alkyl group of the polyether. This prepolymer is then further reacted with another diol where R is small, for example, 1,4-butanediol, to yield a thermoplastic, elastomeric polymer, the properties of which can be tailored by adjusting the proportions of polyether and butane diols. Polymers of this type in grades approved for medical use may be purchased from Dow Chemical, Midland, Mich., under the name Pellethane™. Different hardnesses are available; the softer grades are generally desirable in the present context because they are easier to dissolve and handle. Solvents that may be used to dissolve polyurethanes include tetrahydrofuran (THF), dimethylsulfoxide (DMSO), and N,N-dimethylformamide (DMF). It is usually desirable to make highly concentrated solutions of polyurethane in the solvent of choice, so that the quantity of solvent that has to be evaporated is minimized.

Other polymers that can exhibit equivalent monolith forming and nicotine flux characteristics are intended to be within the scope of the present invention. Examples that might be used, depending on the desired nicotine load, film thickness, etc. include methacrylate polymers such as polymethyl methacrylate or polybutyl methacrylate, or ethylene-acrylic acid polymers, or functional equivalents thereof.

3. The Adhesive Layer

In use, the patches of the present invention may be held in contact with the patient's skin in a variety of ways, such as by means of a porous or nonporous overlay coated wholly or partly with adhesive, by an adhesive layer between the patch and skin, or by an annulus of adhesive around the periphery of the patch. Of course, the mixed reservoir/ monolith embodiments with adhesive medical tapes do not require additional adhesive.

If an adhesive layer is to be included as an integral part of the patch, the adhesive should be nicotine compatible and permit a useful nicotine flux. In addition, the adhesive should satisfy the general criteria for adhesives used for transdermal patches in terms of biocompatibility, ease of application and removal, etc.

Suitable adhesives for use in the practice of the invention include pressure-sensitive adhesives approved for medical use. Amine-resistant types are preferred, so that the adhesive will not be attacked by the nicotine. For example, acrylate-type adhesives with amine resistance can be used. Alternatively, a range of silicone-based amine-resistant medical adhesives is offered by Dow Corning under the trade name BIO PSA. The adhesive layer can be cast directly onto the skin-facing side of the membrane or monolith as a thin film. Alternatively, medical adhesive tape, with or without nicotine-flux controlling properties, may be used.

4. The Peel Strip

Loss of nicotine from the patch after manufacture should be kept to a minimum. Normally, the skin-facing side of the patch will be covered with a peel strip until the patch is used. As stressed throughout, nicotine is volatile, and retention of the nicotine load within the patch during storage requires that the outer patch layers be extremely nicotine-resistant and nicotine-impermeable. The peel strip therefore should possess the same properties as the backing layer, and the same materials are preferred.

5. A Preferred Embodiment

According to a particularly preferred embodiment, the transdermal nicotine patch will comprise a rounded-rectangular, "skin tone" colored patch on a clear, rectangular release liner. More specifically, the patch will comprise a flexible, occlusive film backing, a multilaminate matrix containing nicotine, a skin adhesive layer, and a protective release liner. The nicotine matrix typically will comprise nicotine, an anti-oxidant, preferably butylated hydroxyl toluene (BHT), and an acrylate-based adhesive. The skin adhesive layer typically will comprise an acrylate-based, pressure-sensitive adhesive.

Typically, these patches will be produced by first producing a casting solution of nicotine, a solubilized acrylic pressure-sensitive adhesive, and a preservative, such as an anti-oxidant. The casting solution is then coated onto a backing material, for example a polyester film laminate, which is then passed through an oven where the adhesive is dried. The coated backing web is laminated onto a prepared adhesive/release liner laminate comprising acrylic resin adhesive solids and a silicone-coated, polyester release liner. The final product is then cut into individual patches. These patches can be individually packaged in heat-sealed laminate pouches.

B. The Reservoir System

Figure 3:
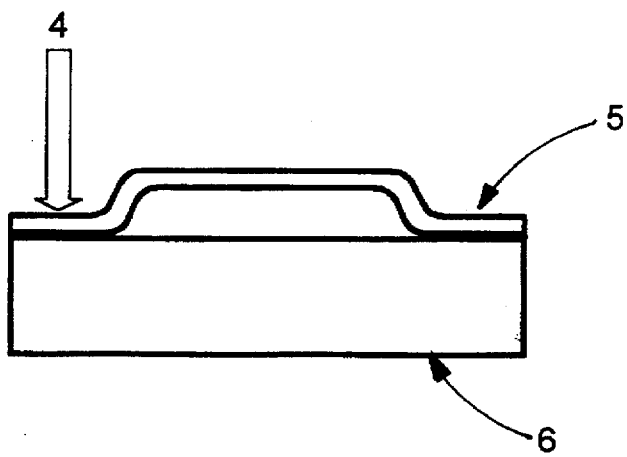
FIG. 3 shows an embodiment of the invention including an impermeable backing (2), a nicotine depot (5), and a rate-controlling polymer membrane (6).

Another embodiment of the invention is shown in FIG. 3. Referring now to this figure, the nicotine dispensing patch, 4, comprises an impermeable backing layer, 2, a nicotine reservoir, 5, and a polymer membrane, 6. The backing layer may be the same as that used for the monolith embodiment described above.

1. The Reservoir

The reservoir may take various forms, for example, pure nicotine, nicotine diluted with a liquid or gelled carrier, or nicotine contained within the pores of a microporous matrix. These reservoir systems are distinguished from the monolith embodiments of FIG. 2 in that the function of the reservoir layer is to be a depot for the nicotine and to keep it in good contact with the membrane layer. The reservoir layer does not contribute to any measurable extent to the rate-controlling mechanism. To discourage tampering with the patch, or misuse of the contents, it may be desirable to mix the nicotine with other materials as described in U.S. Pat. No. 4,597,961 to Etscorn, incorporated herein by reference.

If the patch is to be loaded with a comparatively small quantity of nicotine, then the nicotine can be conveniently kept in contact with the membrane layer by holding it in the pores of a microporous matrix. Applicants have found that a disk of microporous nylon can be used. The disk also decreases the user's risk of exposure to a high dose of nicotine should the patch become accidentally ruptured.

2. The Membrane Layer

The polymer membrane layer, 6, is the rate-controlling means that regulates the flux of nicotine from the patch to the skin. The criteria for selection of a suitable material are those discussed in the background section above, namely resistance to attack by nicotine, and possession of an appropriate permeability for nicotine. The polymer chosen should also be compatible with the other components, and workable by standard techniques that are used in fabrication of the patch, such as casting or heat sealing.

Dense nonporous membranes have a substantial advantage over microporous materials. Microporous membranes release the contents of the patch by pore flow. Thus, in areas of the pores, the skin is exposed to raw nicotine. Also, in the case of a volatile liquid such as nicotine, flow through the pores occurs rapidly, so that the system is quickly exhausted, and the skin is flooded with excess nicotine for the life of the patch. In contrast, diffusion of nicotine through a nonporous film takes place by dissolution of the nicotine in the film, followed by diffusion under a concentration gradient. By selecting materials with suitable permeabilities, and making a membrane of appropriate thickness, it is possible, as taught by applicant, to tailor systems that can release their nicotine load gradually over 12 or 24 hours in a safe, controlled fashion.

Furthermore, the solution/diffusion mechanism protects the patient's skin from exposure to excess amounts of raw nicotine. Based on extensive experimentation, Applicants believe that preferred membrane polymers are low, medium, or high density commercial polyethylenes. Particularly suitable are the grades obtainable under the trade name Sclair-film™ from DuPont Canada or those from Consolidated Thermoplastics. The 3M Corporation also manufactures a line of polyethylene membranes faced with adhesive tapes that are very suitable. Other possible membrane materials are polyamides, such as nylon 6,6, or some grades of ethylene vinyl acetate copolymers. Functional equivalents of these are intended to be within the scope of the invention.

The membrane layer may be formed by preparing a solution of the chosen polymer in an organic solvent, casting on a glass plate or in a mold, and drying to evaporate the solvent. The thickness of the finished film is tailored to give the desired nicotine flux. In general, membranes used in transdermal patches have thicknesses ranging from about 5 mu m to about 200 mu m.

Alternatively, it may be possible to purchase the membrane already in film form. This type of transdermal patch may be prepared by heat-sealing the backing to the membrane layer around the perimeter of the patch. The nicotine formulation may be added either before or after heat sealing. If the formulation is added before heat sealing, it is convenient to shape the backing so as to form a cavity for retention of the nicotine, or to gel the nicotine. If the formulation is incorporated after heat sealing, the nicotine may be injected into the pouch formed by the heat sealing process, and the injection hole sealed.

As discussed for the monolithic embodiments, the patches of the present invention may frequently be required to hold a total nicotine load that is 50% or more of the lethal dose. It is therefore important that the patches be able to control the nicotine flux to the skin within safe limits at all times. In this regard, reservoir-type embodiments have an advantage over the monolith systems. The advantage is that, so long as undiluted nicotine remains in contact with the reservoir side of the membrane, the nicotine flux through the membrane remains relatively constant over the life of the patch.

Monolith-type embodiments, on the other hand, often exhibit a falling flux with time, as the portion of the monolith closer to the skin becomes depleted of drug. As discussed above, these kinds of considerations matter more when dispensing nicotine than with many other substances. Suppose that a transdermal patch, tested in vitro, delivers a substantial fraction of its total drug load during the first few hours, at a flux several times higher than the average skin permeation rate. The in vitro flux then falls off to levels that are well below the average skin permeation rate until the patch is exhausted. When this patch is applied to the user, the skin will be saturated with drug and the drug will pass through the skin at a rate determined by that user's skin permeability.

Typically a "depot" of drug will build up in the skin, and the drug will gradually reach the systemic circulation from this depot. Individuals with unusually high skin permeabilities will build up a larger skin depot faster than those with low skin permeabilities. For drugs that are less toxic than nicotine, less irritating to the skin, and/or have much lower skin permeabilities, this "skin depot" phenomenon may be perfectly acceptable, or even preferable, since it tends to balance out the falling flux from the patch.

Many transdermal patches currently available exhibit this effect and function satisfactorily in this way. However, for nicotine, the situation is different. A patch that can avoid this high initial drug burst, with consequent skin irritation or risk of overdose, is desirable. Any initial flux from the patch should not exceed a maximum of 2 mg/cm$^2$ h, and more preferably should not exceed 1 mg/cm$^2$·h. Any flux this high should never be sustained for more than 4–5 hours, and preferably should not be sustained for more than 1–2 hours. Depending on the drug load, the skin permeability of the patient, and the drug flux required, it may be easier to stay within this limit with a reservoir-type patch. The risk of accidental overdose if the patch is damaged or ingested, however, is minimized with monolithic embodiments. There will therefore be circumstances where one or the other type of patch is preferably indicated.

C. The Mixed Monolith Reservoir System

Figure 4:
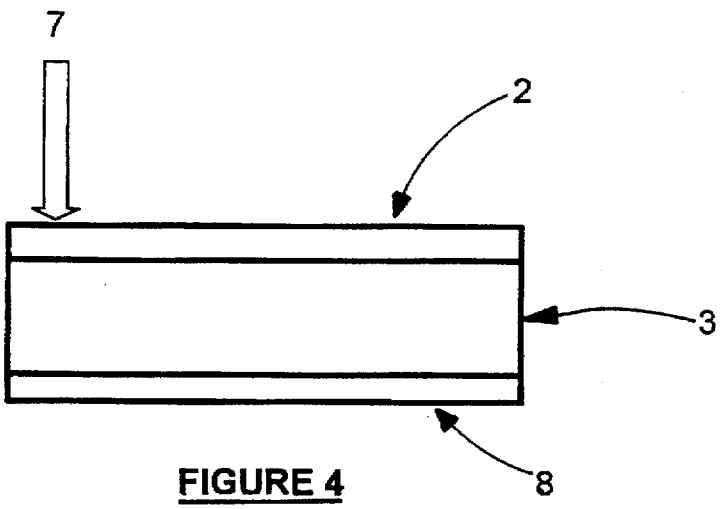
FIG. 4 shows an embodiment of the invention including an impermeable backing (2), a monolithic nicotine-containing matrix (3), and a polymer membrane (8).

The embodiment shown in FIG. 4 exploits the advantages of both reservoir and monolith systems. Referring now to this figure, the nicotine dispensing patch, 7, comprises an impermeable backing layer, 2, a monolithic matrix layer, 3, and a polymer membrane layer, 8. The backing and monolith layers are selected and prepared as described for the embodiment of FIG. 2.

The membrane layer may be selected and prepared as described for the embodiment of FIG. 2. Alternatively, and preferably, the membrane layer may take the form of a double-sided medical adhesive tape, which may be conveniently be attached to the finished monolith on the skin-facing side. If the tape contains a polymer backbone material that offers resistance to nicotine permeation, then this adhesive layer may have a nicotine permeability of the same order or less than the monolith material, so that the adhesive layer serves as a thin membrane limiting flux of nicotine from the patch.

The system functions as a mixed monolith reservoir system, where the nicotine release characteristics depend both on the monolith layer and the membrane polymer. The preferred tapes for use in this way are those with a polyethylene backbone, such as 3M-1509, a 75 mu m thick medical tape containing medium density polyethylene, and 3M-1512, a 38 mu m thick polyethylene tape, both available from 3M Company. The additional resistance to permeation created by the tape assists in holding the nicotine load in the patch and moderates the initial high drug flux.

This embodiment is particularly useful in cases where the percentage nicotine load of the monolith is high, say more than about 30 wt %, or where the total nicotine load is high, say 30 mg or more. Systems with this amount of nicotine are more likely to exhibit a large burst effect on initial application to the patient's skin than those with low nicotine content. The additional resistance of the membrane/tape layer is useful in keeping the initial nicotine flux within therapeutically acceptable levels.

Other advantages associated with this embodiment include a nicotine activity representative of the concentration of nicotine in the monolith, so that skin irritation and adhesive degradation are minimized. The risk of an overdose of nicotine is reduced, because the monolith cannot release its nicotine load in a single burst if the patch is damaged or even swallowed.

D. Other Embodiments

Other embodiments of the present invention will utilize the transdermal nicotine patches described, for example, in U.S. Pat. Nos. 4,597,961, 5,004,610, 4,946,853, and 4,920,989, each of which is expressly incorporated herein by reference. More specifically, according to one embodiment, a transdermal nicotine patch similar to the PROSTEP$^{SM}$ will be employed. This patch comprises, proceeding from the visible outer surface toward the inner surface attached to the skin, (1) a foam tape and pressure-sensitive acrylate adhesive; (2) backing foil, gelatin, and low density polyethylene; (3) nicotine-gel matrix; (4) protective foil with well, and (5) release liner.

Alternatively, a nicotine patch similar to the Habitrol$^{SM}$ patch can be used. This patch comprises, proceeding from the visible outer surface toward the inner surface attached to the skin, (1) an aluminized-backing film; (2) a pressure-sensitive acrylate adhesive; (3) a layer containing a methacrylic acid copolymer solution of nicotine dispersed in a pad of nonwoven viscose and cotton; (4) an adhesive layer similar in composition to layer (2) above; and (5) a protective aluminized release liner.

Other embodiments will employ a nicotine patch similar to the Nicoderm® nicotine transdermal system, available from ALZA Corporation, Palo Alto, Calif. This patch is a multilayered rectangular film containing nicotine as the active agent. Proceeding from the visible surface toward the surface attached to the skin are (1) an occlusive backing, e.g., polyethylene/aluminum/polyester/ethylene-vinyl acetate copolymer; (2) a drug reservoir containing nicotine, typically in an ethylene-vinyl acetate copolymer matrix; (3) a rate-controlling membrane, such as polyethylene; (4) a polyisobutylene adhesive; and (5) a protective liner that covers the adhesive layer and must be removed before application to the skin.

E. Patch Specifications

The transdermal nicotine patch provides a base line or steady state nicotine level to the patient. The total amount of nicotine released by the patch during the period of use will vary depending on the user's body size, history of exposure to nicotine, and response to treatment, but will be roughly in the range of 5–60 mg. In general, this dosage will maintain the nicotine blood level at a baseline level of between 5 to 35 ng/mL nicotine, and more preferably between 10–20 ng/mL, which is believed to be the preferred steady-state blood level for optimal therapy in most patients.

General guidelines for patch design must ensure that the patient is protected at all times from toxic doses of nicotine, and must also ensure that the patient receives a dose of nicotine that will be effective for smoking cessation therapy. The in vitro flux from any individual patch used for the intended therapy should remain below about 800 mu g/cm$^2$·h, preferably below 600 mu g/cm$^2$·h, and more preferably below 400 mu g/cm$^2$·h during the life of the patch. Staying within these limits ensures that a patient with unusually permeable skin can never receive a toxic dose.

The size of the patch will vary according to the amount of nicotine to be delivered. To deliver 25 mg in a 24-hour period, the patch would have a skin-contacting area of about 15–30 cm$^2$. To maximize patient acceptance and compliance, and to minimize any skin irritation, the patch size should not exceed about 45 cm$^2$ maximum skin covering area. With the systems and release characteristics taught by applicant, it should be possible to keep the patch size in the range 1–50 cm$^2$, preferably 20–35 cm$^2$.

IV. The Transmucosal Administration of Nicotine

The present invention provides for the transmucosal administration of nicotine, before, during, or after the transdermal delivery of nicotine. Transmucosal administration includes the delivery of nicotine through the oral mucosa, such as the sublingual and buccal mucosa, as well as through other membranes, including rectal, vaginal, and nasal membranes. These latter routes of administration are commonly used alternatives to oral administration, as they avoid the potential inconveniences of oral drug delivery, such as a patient's inability to swallow and gastrointestinal side effects, and they offer direct access to the site of absorption, thereby generally increasing the rate and extent of absorption.

Moreover, rectal drug administration has the advantage of minimizing or avoiding hepatic first pass metabolism, thereby increasing a drug's bioavailability. However, systemic bioavailability for rectal dosage forms does seem to depend on a number of factors, including the site of absorption in the rectum and rectal motility. Similarly, delivery of drugs by the nasal route offers an attractive alternative to oral administration by virtue of the relatively rapid drug absorption, possible bypassing of presystemic clearance, and relative ease of administration. Intravaginal drug administration offers the advantages of minimized systemic side effects and rapid drug absorption. Therefore, drugs administered intravaginally have increased bioavailability over their orally administered counterparts, because of a reduced first pass metabolism.

A. Delivery through the Oral Mucosa

According to a particularly preferred embodiment, transmucosal administration of nicotine will comprise oral administration (i.e, sublingual and buccal). This form of drug delivery provides for an efficient entry of active substances to the systemic circulation and reduces immediate metabolism by the liver and intestinal wall flora. Oral drug dosage forms (e.g., lozenge, capsule, gum, tablet, suppository, ointment, gel, pessary, membrane, and powder) are typically held in contact with the mucosal membrane and disintegrate and/or dissolve rapidly to allow immediate systemic absorption. This term includes, but is not limited to, lozenges, capsules, tablets, and gum.

The methods of manufacture of these formulations are known in the art, and include but are not limited to, the addition of the pharmacological agent to a pre-manufactured tablet; cold compression of an inert filler, a binder, and either a pharmacological agent or a substance containing the agent (as described in U.S. Pat. No. 4,806,356); and encapsulation. Another oral formulation is one that can be applied with an adhesive, such as the cellulose derivative, hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa.

Preferably, the orally administrable nicotine formulation of the present invention will consist of any lozenge, tablet, capsule, or gum formulation that delivers nicotine rapidly through the oral mucosa cavity, and preferably through the buccal and/or sublingual mucosa. The nicotine form that is added or incorporated into the nicotine formulations may be pure nicotine or any compound thereof. The method of manufacture of these formulations may be any suitable method known in the art, including but not limited to the addition of a nicotine compound to premanufactured tablets; cold compression of an inert filler, a binder, and either pure nicotine or a nicotine-containing substance (as described in U.S. Pat. No. 4,806,356, herein incorporated by reference); encapsulation of nicotine or a nicotine compound; and incorporation of nicotine bound to a cation exchange resin, for example, as in a chewing gum (as described in U.S. Pat. Nos. 3,877,468 and 3,901,248, herein incorporated by reference).

Another oral formulation that is disclosed in the present invention is one that can be applied with an adhesive, such as the cellulose derivative, hydroxypropyl cellulose, to the oral mucosa, for example as described in U.S. Pat. No. 4,940,587. This buccal adhesive formulation, when applied to the buccal mucosa, allows for controlled release of nicotine into the mouth and through the buccal mucosa.

In a particularly preferred embodiment, the orally administrable nicotine formulation is a nicotine lozenge that delivers nicotine to the buccal cavity, comprising nicotine dispersed in an absorbent excipient and a nonnutritive sweetener. See U.S. Pat. No. 5,549,906, which is hereby incorporated by reference. The lozenge is preferably held from 2–10 minutes in the mouth as it dissolves completely and releases nicotine into the mouth, and the dissolved nicotine solution is held in the mouth for as long as possible so that the nicotine is absorbed through the buccal mucosa.

In another preferred embodiment, the orally administrable nicotine formulation comprises a nicotine gum, for example, the nicotine gum that is commercially available from Merrell-Dow of Cincinnati, Ohio under the trademark Nicorette.

Nicotine is a heterocyclic compound that exists in both a free base and a salt form. The free base is extremely volatile and is absorbed readily through mucous membranes and intact skin. The major problems reported for products based on nicotine free base originate from the volatility of the nicotine, its acrid, burning taste, the irritating sensation on the mucous membranes, and the decomposition of nicotine in the presence of oxygen. Previously, these problems have been alleviated, in part, through the use of nicotine's salt form, i.e., an acid addition salt or metal salt.

Surprisingly, the orally administrable nicotine formulations described herein can be produced from either the free base or a pharmaceutically acceptable acid addition salt thereof, or any combination thereof. In an exemplary embodiment, nicotine, i.e., the free base form of nicotine, is used to produce a nicotine lozenge.

In any formulation used, the orally administrable nicotine formulation contains fairly low doses of nicotine, preferably less than about 5 mg, and most preferably from about 0.5 to 4.0 mg, and in the case of nicotine lozenges or tablets, most preferably from about 0.5 to about 2.0 mg, to avoid accidental overdosage by swallowing the formulation intact. In addition, high doses are not required because the purpose of the nicotine formulation is to provide a transient blood level peak of nicotine.

Use of the orally administrable nicotine formulation will result in transient nicotine blood level peaks that are at least 5 ng/mL higher, and more preferably at least 10 ng/mL higher, than the consistent nicotine blood level provided by the transdermal nicotine system. Use of the orally administrable nicotine formulation will result in this transient nicotine blood level peak from about 2 to 30 minutes, preferably from about 2 to 20 minutes, and more preferably from about 2 to 10 minutes, after the oral formulation is placed in the mouth.

The orally administrable nicotine formulation preferably is buffered to aid in the oral absorption of nicotine. A preferred formulation is at a pH of 6.8–11. Preferred buffered formulations will include sodium carbonate, sodium phosphate, calcium carbonate, magnesium hydroxide, magnesium carbonate, aluminum hydroxide, and other substances known to those skilled in the art. The orally administrable nicotine formulation may contain a candy taste, such as a mint or other flavor, to mask the taste of nicotine.

B. The Nicotine Lozenge

1. The Absorbent Excipient

According to a particularly preferred embodiment, the nicotine is dispersed in an absorbent excipient to form a nicotine lozenge. Absorbent excipients are pharmaceutically acceptable substances that are capable 1) of reducing the volatility of the nicotine, for example, through absorption or by the incorporation of nicotine, such as in an inclusion complex, and 2) of being compressed into a lozenge or tablet. Suitable absorbent excipients include, but are not limited to, mannitol; cyclodextrins, including α-, β-, and γ-cyclodextrin, as well as derivatives of cyclodextrins, such as trimethyl-β-cyclodextrin, dimethyl-β-cyclodextrin, hydroxyethyl-β-cyclodextrin, and hydroxypropyl-β-cyclodextrin; silica preparations, such as the synthetic silica formulation marketed under the trade name Syloid™ by W. R. Grace Limited of North Dale House, North Circular Road, London; cellulosic materials, such as Avicel microcellulose manufactured by FMC Corporation; and other conventional binders and fillers used in the food industry, such as acacia powder, gelatin, gum arabic, and sorbitol.

According to some embodiments, the absorbent excipient will serve more than one role in the lozenge formulation. For example, mannitol can function as both a nonnutritive sweetener and an absorbent excipient. Similarly, the absorbent excipient can serve as a flavorant, buffering agent, lubricant, or other component of the lozenge.

The absorbent excipient is typically present in an amount between about 5 and 25% by weight (wt %), preferably in an amount between about 5 and 20 wt %, and more preferably in an amount between about 5 and 15 wt %.

In a preferred embodiment, the absorbent excipient comprises mannitol or β-cyclodextrin.

2. The Nonnutritive Sweetener

The nicotine lozenge will also contain a nonnutritive sweetener. Since nicotine has an acrid, burning taste, the choice of a sweetener for a nicotine lozenge can be critical, for many patients do not find the taste of nicotine palatable in lozenge form. Typically, a nonnutritive sweetener or more preferably, a combination of sweeteners will be utilized in the lozenges described herein.

A nonnutritive sweetener is a synthetic or natural sugar substitute whose sweetness is higher than or comparable to with sucrose. Table I lists examples of nonnutritive sweeteners and their relative sweetness values.

TABLE I

| Nonnutritive Sweeteners | | | |
|---|---|---|---|
| Sweetener | Sweetness[1] | Sweetener | Sweetness[1] |
| Saccharin | 400–500 | Invert sugar | 1.1–1.2 |
| Cyclamate | 30–40 | Palantinose | 0.4–0.5 |
| Aspartame | 100–200 | Xylitol | 1.0 |
| Acesulfame | 200 | Sorbitol | 0.5–0.6 |
| Monellin | 2500 | Mannitol | 0.4–0.6 |
| Neohesperidine | 1000 | Maltitol | 0.7–0.9 |
| Palatinit | 0.4–0.5 | — | — |

[1]Sucrose = 1.0

Thus, the nonnutritive sweetener should have a relative sweetness value between about 0.4 and 2500, as compared with sucrose, more typically between about 0.4 and 500, preferably between about 0.4 and 200, and more preferably, between about 0.4 and 2. See Makinen (1988) *Oral Health* 78:57–66, which is incorporated herein by reference.

In a preferred embodiment, the nonnutritive sweetener is also noncariogenic. The cariogenicity of a substance is dependent upon its susceptibility to fermentation by Streptococcus mutans and other oral microorganisms. Dental researchers have long recognized that fermentable sweeteners such as sucrose, glucose, starch, and corn syrup are cariogenic or caries causing. The polyol nonnutritive sweeteners, such as xylitol, sorbitol, fructose, invert sugar, palantinose, mannitol, maltitol, palatinit, and ammonium glycyrrhizinate, however, are generally not fermented to any significant degree and are less cariogenic than sucrose. See Olinger presented at the Interphex-USA Conference/Exhibition, New York; May 8–11, 1990.

More specifically, the ability of xylitol to inhibit the development of new caries has been demonstrated in numerous in vitro and in vivo studies. For example, field trials of oral products containing xylitol have suggested that substitution of sucrose by xylitol in products such as chewing gum may aid in prevention of dental caries (see Söderling, E., and Scheinin, A., *Proc. Finn. Dent. Soc.* 1991, 87(2), 217–229). Studies have also revealed that when xylitol-containing confections are consumed as part of a normal diet, in conjunction with accepted oral hygiene practices, new caries incidence is reduced by about 50% to as high as 80%. See Olinger supra.

Moreover, the literature suggests that nonnutritive sweeteners, and particularly xylitol, may be useful as a sugar substitute for weight control, (see U.S. Pat. No. 3,717,711), which is clearly a major concern for people who are quitting smoking. In addition, xylitol as been shown to prolong gastric emptying and decrease food intake in humans. See Shafer et al. (1987) *Am. J. Clin. Nutr.* 45:744–47. Likewise, because xylitol is not metabolized as a sugar, it has value for use with people who must restrict their sugar intake, such as diabetics (see Maukinen, K., *Oral Health* 1988, 78(9), page 60).

Xylitol also has a cooling effect when it dissolves in the mouth, due to its negative heat of solution. Xylitol's heat of solution is –36.6 cal/g, compared to –28.9 cal/g for mannitol, –26.6 cal/g for sorbitol, and –4.3 cal/g for sucrose (see Olinger, P. M., presented at the Interphex. USA Conference/Exhibition, New York; May 8–11, 1990). Therefore, xylitol is an excellent choice for a sweetener and excipient in a lozenge that needs to be held in the mouth for an extended period of time, and that needs to be taken frequently every day for maximum therapeutic effect.

Frequently a combination of nonnutritive sweeteners will be used. According to one embodiment, a sweetener with temporal sensory properties similar to that of sucrose (i.e., an appearance time of about 4 seconds and an extinction time of 13 seconds, e.g., some of the polyol sweeteners, saccharin, cyclamate and aspartame) will be combined with a sweetener whose sweetness develops slower or persists longer. For example, ammonium glycyrrhizinate, a nonnutritive sweetener with a slight licorice taste, has a taste onset or appearance time of about 16 seconds for ammonium glycyrrhizinate and a taste persistence or extinction time of 69 seconds. Dubois and Lee (1983) *Chem. Sens.* 7:237–248. Other examples of nonnutritive sweeteners with temporal sensory properties different than that of sucrose include, but are not limited to, neohesperidine dihydrochalcone (appearance time of 9 seconds and an extinction time of 40 seconds) and stevioside (appearance time of 4 seconds and an extinction time of 22 seconds).

In a preferred formulation, the lozenge will contain a nonnutritive, noncariogenic sweetener, such as xylitol, sorbitol, fructose, invert sugar, palantinose, mannitol, maltitol, and palatinit, either alone or in combination with other nonnutritive sweeteners. More preferably, xylitol, either alone or in combination with a nonnutritive sweetener having an extinction time longer than that of sucrose, such as ammonium glycyrrhizinate, neohesperidine dihydrochalcone, or stevioside, will be used. In an exemplary embodiment, the nonnutritive sweetener will comprise xylitol and ammonium glycyrrhizinate.

The nonnutritive sweetener is typically present in an amount between about 50 and 90 wt %, preferably in an amount between about 70 and 90 wt %, and more preferably in an amount between about 80 and 90 wt %.

3. Other Ingredients

The lozenge preferably is a buffered formulation in order to aid in buccal absorption of nicotine. A preferred formulation is at a pH of about 6–11, and preferably at a pH of about 7–9. Preferred buffered formulations will include sodium carbonate, sodium bicarbonate, sodium phosphate, calcium carbonate, magnesium hydroxide, potassium hydroxide, magnesium carbonate, aluminum hydroxide, and other substances known to those skilled in the art, as well as combinations of the aforementioned substances. In a most preferred formulation, the lozenge will contain sodium carbonate and bicarbonate as buffering agents.

The buffering agent(s) should be present in an amount sufficient to adjust the pH of the lozenge to between 6 and 11, typically, between about 0.1 and 25% by weight (wt %), preferably in an amount between about 0.1 and 10 wt %, and more preferably in an amount between about 0.1 and 5 wt %.

In addition, the lozenge may contain a flavorant, for example, a candy taste, such as chocolate, orange, vanilla, and the like; essential oils such as peppermint, spearmint and the like; or other flavor, such as aniseed, eucalyptus, 1-menthol, carvone, anethole and the like, to mask the taste of nicotine. See Hall et al. *Food Technol.* 14:488 (1960); 15:20 (1961); 19:151 (1965); 24:25 (1970); 26:35 (1972); 27:64 (1973); 22:56 (1973); 28:76 (1974); 29:70 (1974) 31:65 (1977); 32:60 (1978); and 33:65 (1979), each of which is incorporated herein by reference. It may also contain tobacco flavor in order to reproduce some of the sensation of smoking for the user. A small amount of colloidal silica (less than about 1 wt %) typically is added to tablets containing tobacco flavor to aid in manufacturing.

Magnesium stearate and/or hydrogenated vegetable oil may also be added to the formulation as lubricants. Typically, the lubricant will be present in an amount between about 0.1 and 25 wt %, preferably in an amount between about 0.1 and 10 wt %, and more preferably in an amount between about 0.1 and 5 wt %.

The lozenges described herein may also contain a variety of other additives. For example, pharmacologically active ingredients such as sodium monofluorophosphate, sodium fluoride, dextranase, mutanase, hinokitiol, allantoin, aminocaproic acid, tranexamic acid, azulene, vitamin E derivatives, sodium chloride and the like can be added at need. More specifically, since the effects of xylitol and fluoride on dental hygiene are additive, the former can significantly enhance the efficacy of traditional fluoride treatments. Thus, according to one embodiment, fluoride, and more particularly sodium monofluorophosphate or sodium fluoride will be incorporated into a lozenge formulation having xylitol as a nonnutritive sweetener.

In addition, the lozenge may be colored with conventional, pharmaceutically acceptable food coloring agents. Other additives that may be incorporated within the lozenges described herein include, but are not limited to, preservatives, antimicrobial agents, and antioxidants.

4. The Method of Manufacture

The method of manufacture of these lozenges may be any suitable method known in the art, including but not limited to, the addition of a nicotine compound to premanufactured tablets; cold compression of an inert filler, a binder, and either pure nicotine or a nicotine-containing substance (as described in U.S. Pat. No. 4,806,356, herein incorporated by reference); and encapsulation of nicotine or a nicotine compound. See U.S. Pat. No. 5,135,753, herein incorporated by reference, for examples of methods of manufacture of various nicotine lozenges, sublingual tablets, and gelatin capsules. In a preferred embodiment, the lozenges are formed using direct compression.

According to another embodiment, an in situ inclusion complex is created with nicotine and β-cyclodextrin using a kneading technique. Specifically, a small amount of a nicotine-water solution is added to cyclodextrin and kneaded or mixed. See Szezetli in *Cyclodextrins and Their Inclusion Complexes*, Akademiai Kiado: Budapest, 1992; p. 109; herein incorporated by reference. This method of forming the nicotine-cyclodextrin inclusion complex is preferred as it minimizes the use of solvents or diluents and thus, eliminates a purification step in the manufacturing process.

A further embodiment of the present invention provides for the production of inclusion complexes of both the nicotine and the flavorant. This embodiment is employed, for example, when an essential oil, or other volatile flavorant, such as carvone or menthol, is used in the lozenge formulation. As in the case of the nicotine inclusion complexes described herein, incorporation of the flavorant into cyclodextrin decreases the volatility of the flavorant and increases formulation stability. In addition, as the flavorant is slowly released from the complex during lozenge administration, the flavorant will "last" longer and thus, offset the acrid taste of the nicotine for longer periods of time.

According to this embodiment, a mixture of the nicotine and the flavorant, and optionally water, is added to the cyclodextrin and kneaded. Alternatively, the nicotine inclusion complex and the flavorant inclusion complex can be prepared separately and then mixed prior to lozenge formulation.

According to another embodiment, a portion of the non-nutritive sweetener, preferably xylitol, is utilized to hard coat the nicotine lozenge. Traditional pan coating techniques can be employed. Typically, weight increases of approximately 35% can be accomplished in less than three hours. See, e.g., Olinger supra.

The lozenges may be packaged in such a manner as to aid in maintaining nicotine stability. Preferred packaging methods include strip lamination in a foil-like material such as Barex®, or packaging in blisters using a Teflon-like material such as Aclar®. See also, Hunt et al. (1991) U.S. Pat. No. 5,077,104.

The lozenges described herein will typically have a weight of between about 70 and 1000 mg and will contain fairly low doses of nicotine, preferably less than 5 mg, and most preferably from 0.5 to 2.0 mg.

C. Nicotine Gum.

According to another embodiment, the orally administrable nicotine formulation will comprise a nicotine chewing gum capable of rapidly delivering nicotine to the oral cavity. One example of such a nicotine gum is Nicorette which is available in two strengths of 2 mg or 4 mg of nicotine bound to an ion-exchange resin and incorporated into a gum base. Release is controlled by the rate and vigor of chewing. The gum is intended to release nicotine over 20–30 minutes in doses similar to those taken by cigarette smokers. However, to produce the rapid release rates suitable for the methods described herein, the nicotine gum should be chewed rapidly and vigorously to produce the desired nicotine plasma levels, i.e., those mimicking cigarette smoking. Other gum formulations may not require such a chewing rate to produce the desired plasma nicotine levels.

Specific examples of the compositions of this invention are set forth below.

D. Other Sites of Transmucosal Administration

For delivery to the nasal membranes, typically an aerosol formulation will be employed. The term "aerosol" includes any gas-borne suspended phase of nicotine which is capable of being inhaled into the bronchioles or nasal passages. Specifically, aerosol includes a gas-borne suspension of droplets of the compositions containing nicotine, as may be produced in a metered dose inhaler or nebulizer, or in a mist sprayer. Aerosol also includes a dry powder composition of a nicotine composition suspended in air or other carrier gas, which may be delivered by insufflation from an inhaler device, for example.

For solutions used in making aerosols, the preferred range of concentration of the nicotine is 0.1–100 milligrams (mg)/milliliter (mL), more preferably 0.1–30 mg/mL, and most preferably, 1–10 mg/mL. Usually the solutions are buffered with a physiologically compatible buffer such as phosphate or bicarbonate. Typically, sodium chloride is added to adjust the osmolarity to the physiological range, preferably within 10% of isotonic. Formulation of such solutions for creating aerosol inhalants is discussed in Remington's Pharmaceutical Sciences, see also, Ganderton and Jones, *Drug Delivery to the Respiratory Tract*, Ellis Horwood (1987); Gonda (1990) *Critical Reviews in Therapeutic Drug Carrier Systems* 6:273–313; and Raeburn et al. (1992) *J. Pharmacol. Toxicol. Methods* 27:143–159.

Solutions of the nicotine containing compositions can be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

For delivery to the rectal or vaginal mucosa, typically the nicotine formulation will comprise a suppository or be incorporated within a vaginal sponge or tampon. Typically, the nicotine containing formulation will be in a semisolid forms such as creams and suppositories. The dosage form should disintegrate rapidly and permit contact of the drug with the mucosa over a relatively large area to promote rapid absorption.

E. Methods for the Transmucosal Administration of Nicotine

Whereas the patch serves to provide a base line or steady state nicotine level, the transmucosal administration of nicotine provides periodic transient blood level peaks of nicotine as an aid in reducing symptoms of craving of nicotine. Typically, the transmucosal administration will be utilized ad libitum by the patient to alleviate cravings for nicotine as they arise. Thus, this method provides for a means for the patient to self-titrate his administration needs.

Again, the desire or need for the transmucosal administration of nicotine (comparable to the desire to smoke cigarettes) typically will vary during any given day and from day to day, as well as from patient to patient. The methods described herein allow the patient to self-administer nicotine in the amounts and at the times when he most feels the craving for nicotine. As nicotine craving is considered by some to be the most consistent and most severe factor in preventing a person from quitting smoking, this ability to self-titrate and thus, stave off the craving for nicotine will increase the efficacy of a smoking cessation program.

A variety of methods can be utilized to assess the craving for nicotine, including but not limited to, the nicotine craving test specified by the *Diagnostic and Statistical Manual of Mental Disorders*, Revised Third Edition (DSM-III-R) (see (1991) *J. Am. Med. Assoc.* 266:3133); the Shiffman-Jarvik Craving Subscale (see O'Connell and Martin (1987) *J. Consult. Clin. Psychol.* 55:367–371 and Steur and Wewers (1989) *ONF* 16:193–198, also describing a parallel visual analog test); West et al. (1984) *Br. J. Addiction* 79:215–219; and Hughes et al. (1984) *Psychopharmacology* 83:82–87, each of which is expressly incorporated herein by reference.

A preferred nicotine craving scale comprises that specified in DSM-III-R. Supra. According to this scale, a subject is asked to rate the severity of his craving for nicotine on a scale between 0 and 4, wherein 0 is none; 1 is slight; 2 is mild; 3 is moderate; and 4 is severe. Using the compositions and methods described herein, the subject should attain at least a one unit, and preferably at least a two unit, decrease in his craving for nicotine as measured by the protocol set forth in DSM-III-R from about 2 to 30 minutes after administration of the oral nicotine formulation. More preferably, the maximum reduction in craving for nicotine will occur from about 2 to 20 minutes, and more preferably from about 2 to 10 minutes after administration of the oral nicotine formulation.

The Shiffman-Jarvik Craving Scale is a six-item, forced-choice, self-report tool that measures cigarette craving. Each item has seven possible responses which correspond to scores ranging from 1 (no craving) to 7 (high craving). A mean score is obtained to determine the respondent's level of craving. A typical craving score measured 48 hours after the initiation of a smoking cessation program is between about 4 and 5; while a two-week follow-up craving scale will typically be between about 3 and 4. Using the compositions and methods described herein, the subject should attain at least a one unit, and preferably at least a two unit, decrease in his craving for nicotine as measured by the protocol set forth in the Shiffman-Jarvik Craving Scale from about 2 to 30 minutes after administration of the oral nicotine formulation. More preferably, the maximum reduction in craving for nicotine will occur from about 2 to 20 minutes, and more preferably from about 2 to 10 minutes after administration of the oral nicotine formulation.

The "craving questionnaire" craving scale employs a five item questionnaire that asks subjects to rate how much they had been missing their cigarettes, how difficult it had been to be without cigarettes, how much they had been aware of not smoking, how pre-occupied they had been with thinking about cigarettes, and how much they had craved their cigarettes. The subject responds to each question with a number between 1 and 3, where 1 is low and 3 is high. The ratings are combined to give a single craving score. According to this craving scale, a combined score of between about 9 and 12 is typical. Using the compositions and methods described herein, the subject should attain at least a three unit, and preferably at least a four unit, decrease in his craving for nicotine as measured by the protocol set forth for use with this craving questionnaire from about 2 to 30 minutes after administration of the oral nicotine formulation. More preferably, the maximum reduction in craving for nicotine will occur from about 2 to 20 minutes, and more preferably from about 2 to 10 minutes after administration of the oral nicotine formulation.

When the transmucosal administration of nicotine is accomplished through the oral mucosa, the nicotine formulations should be administered without holding any other substance, such as food or beverage, in the mouth. It is particularly important that acidic substances or beverages such as fruits, coffee, tea, or fruit juices are not consumed immediately or concurrently with the oral nicotine formulations, in order to insure that a basic environment is maintained within the mouth.

According to a particularly preferred embodiment, a nicotine lozenge or tablet is held from 2–10 minutes in the mouth as it dissolves completely and releases nicotine into the mouth, and the dissolved nicotine solution is held in the mouth for as long as possible so that the nicotine is absorbed through the buccal mucosa. According to another preferred embodiment, a nicotine containing gum is vigorously chewed to release nicotine into the oral cavity.

Example 39 describes a protocol for measuring nicotine blood levels in patients following the transmucosal administration of nicotine. The nicotine blood levels in these patient should closely mimic the transient peak levels of a cigarette smoker. For example, use of the lozenge will result in transient nicotine blood level peaks that are in the range of 15 to 35 ng/mL, and more preferably in the range of 20 to 30 ng/mL.

Figure 13:
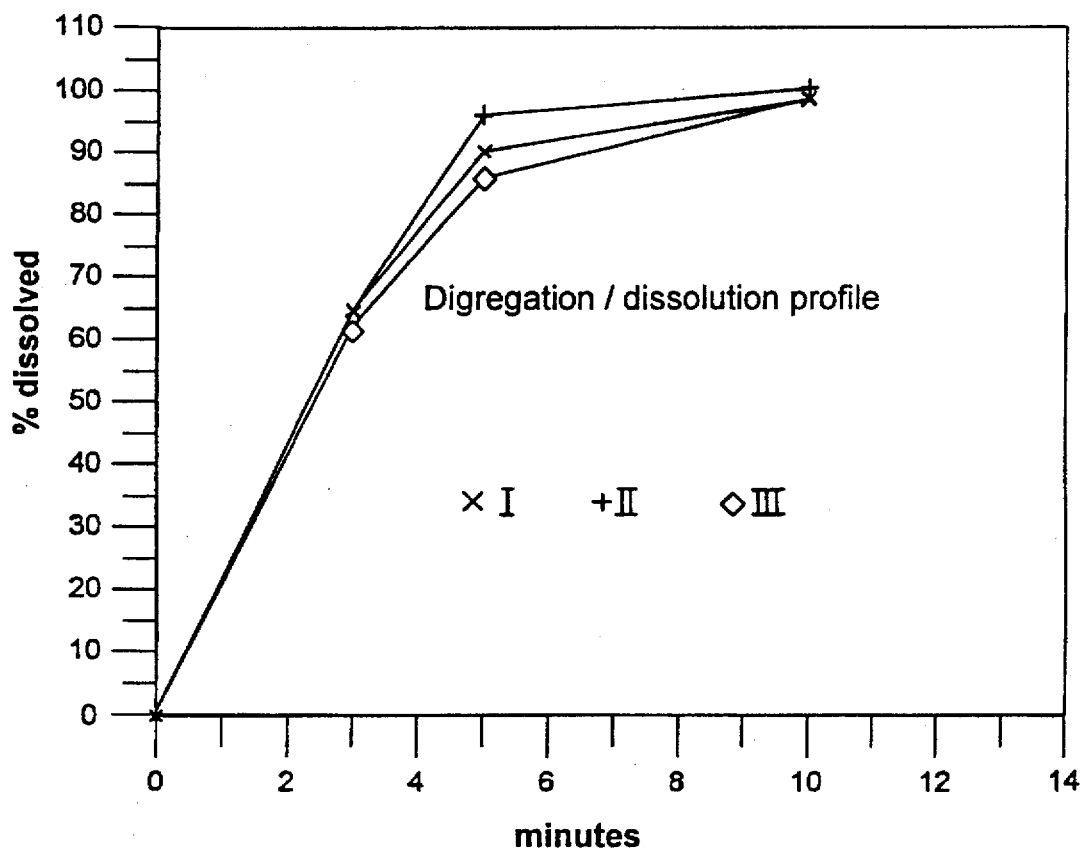
FIG. 13 is a graph of the disintegration/dissolution profiles (weight % dissolved) of three different lozenge formulations, each containing 1 mg nicotine, as a function of time (minutes).

The transmucosal administration of nicotine will result in this transient nicotine blood level peak from about 2 to 30 minutes, preferably from about 2 to 20 minutes, and more preferably from about 2 to 10 minutes, after the formulation is administered. For example, FIG. 13 presents the disintegration/dissolution profiles of the three nicotine lozenge formulations described in Examples 34–36 (Formulation 1 contains nicotine, mannitol, xylitol, mint flavor, and other excipients; Formulation 2 contains nicotine, mannitol, xylitol, tobacco flavor, and other excipients; and Formulation 3 contains nicotine, cyclodextrin, xylitol, and mint flavor). As shown in FIG. 13, lozenges formulated according to the present invention will be at least 60% dissolved after 3 minutes in the mouth, at least 80% dissolved after 5 minutes, and approximately 100% dissolved after 10 minutes.

IV. The Transdermal and Transmucosal Administration of Nicotine

When smoking a cigarette, the smoker receives an initial burst of nicotine into the bloodstream, which then rapidly declines. The urge to smoke increases as the nicotine level continues to fall below a given point in the blood level, a point which can vary with each smoker. However, it has been shown that the normal plasma trough level associated with normal smoking is approximately 5–15 ng/mL within one hour of first smoking. At the time of smoking the plasma level is between 15 ng/mL and 30 ng/mL and the natural urge to smoke is thereby suppressed. When nicotine levels fall to a level of 10 ng/mL or less, nicotine intake is required to suppress the smoking urge.

Although the nicotine plasma levels required to suppress smoking are fairly consistent between smokers, smokers vary widely in their frequency of smoking, i.e., how often the smoking urge occurs. More specifically, nicotine cravings depend, in part, upon daily stress patterns, sleep and eating habits and body weight, previous smoking levels, demographic factors, behavioral factors, race-ethnicity, culture, and the like. See Sachs and Leischow (1991) *Clinics in Chest Medicine* 12:769–791.

A subject's frequency of smoking can be quantified using an eight-question scale, termed the Fagerstrom Nicotine Tolerance Scale (see Fagerstrom (1978) *Addict. Behav.* 3:235–241 and Sachs (1986) Clinics in Geriatric Medicine 2:337–362) which provides a relative index of the degree of physical dependency that a patient has for nicotine. This test is shown below in Table II.

TABLE II

| Fagerstrom Nicotine Tolerance Scale | | | |
|---|---|---|---|
| | A | B | C |
| How soon after you wake up do you smoke your first cigarette? | After 30 min | Within 30 min | |
| Do you find it difficult to refrain from smoking in places where it is forbidden, such as the library, theater, doctor's office? | No | Yes | |
| Which of all the cigarettes you smoke in a day is the most satisfying one? | Any other than the first one in the morning | The first one in the morning | |
| How many cigarettes a day do you smoke? | 1–15 | 16–25 | More than 26 |

TABLE II-continued

| Fagerstrom Nicotine Tolerance Scale | | | |
|---|---|---|---|
| | A | B | C |
| Do you smoke more during the morning than during the rest of the day? | No | Yes | |
| Do you smoke when you are so ill that you are in bed most of the day? | No | Yes | |
| Does the brand you smoke have a low, medium, or high nicotine content? | Low | Medium | High |
| How often do you inhale the smoke from your cigarettes? | Never | Sometimes | Always |

Points are assigned as follows: 0 points for each answer in column 1; 1 point for each answer in column B; and 2 points for each answer in column C. The points are totaled to yield the nicotine tolerance scale. The highest possible score is 11. Patients who score 7 or more are considered to be highly dependent on nicotine. Patients who score less than 6 have a low nicotine dependence.

Thus, the objective for any smoking cessation therapy involving nicotine administration should be the rapid attainment of the appropriate nicotine plasma levels at the necessary frequency of administration for the individual patient, while sustaining a minimum steady state or base line level of nicotine plasma level. The present invention fulfills this objective through the use of a transdermal nicotine patch in combination with the transmucosal administration of nicotine, and preferably the administration of nicotine through the oral mucosa, and most preferably, with nicotine lozenges. The transdermal patch and the transmucosal administration of nicotine operate in a complimentary manner with the transdermal patch providing the steady-state systemic levels of nicotine in the bloodstream to which the smoker has become accustomed, whereas the transmucosal administration of nicotine provides for the rapid attainment of the transient levels of nicotine that mimic cigarette smoking and are required to alleviate nicotine craving.

Moreover, in contrast to previous smoking cessation therapies that can be characterized as a "one size fits all" approach in that these therapies did not take into account the many factors which may contribute to nicotine craving, the compositions and methods described herein allow for an individualized approach to smoking cessation therapy. Specifically, the total amount of nicotine delivered, the delivery mode, i.e., via patch or transmucosal delivery method and regimen, i.e., the order of administration and duration of use of either the patch and/or the transmucosal delivery formulation, can be varied to take into account the patient's needs, e.g., the therapeutic indication, the patient's age and body weight, and the degree of nicotine dependency displayed by the patient.

For example, according to one embodiment, the transdermal patch and transmucosal administration of nicotine are first used concurrently and simultaneously for a period of from about 3 to 12 weeks, and preferably from about 4 to 8 weeks, followed by a period of from about 3 to 12 weeks, preferably from about 4 to 8 weeks, and most preferably from about 4 to 6 weeks, in which only the patch or only the transmucosal nicotine formulation is used.

Other embodiments will employ different dosage levels of either the patch and/or the transmucosal nicotine formulation to suit the needs of those patients with either a relatively high or low nicotine dependency. For example, a smoking cessation program for heavy smokers, i.e., those smokers having a score of 7 or more on the Fagerstrom test, will typically consist of three phases. During the initial phase, a high dosage nicotine transdermal patch, typically, with a high loading of nicotine in the range of about 30–60 mg, and preferably, about 40–45 mg, is administered for a period of from about 4 to 8 weeks. Typically, transmucosal administration of nicotine will be used in conjunction with this high dosage patch. Subsequently, a transdermal patch with a lower loading of nicotine, typically in the range of about 10–30 mg, and preferably, about 20–25 mg, and again, the transmucosal administration of nicotine will be used in combination for a period of from about 4 to 8 weeks. Finally, for a period of from about 4 to 6 weeks, either the patch or the transmucosal administration of nicotine may be used alone.

A similar smoking cessation program can be developed for the moderate smoker, i.e., those scoring 6 or less on the Fagerstrom test. For example, during the initial phase, a transdermal patch with a moderate loading of nicotine, typically in the range of about 10–40 mg, and preferably, about 25–30 mg, is administered in conjunction with the transmucosal administration of nicotine. The second phase of this smoking cessation program will consist of administration of a lower dosage transdermal patch, typically containing nicotine in the range of about 10–30 mg, and preferably, about 20–25 mg, optionally, with the transmucosal administration of nicotine, will be used for a period of from about 4 to 8 weeks. During the final phase or weaning period, either the patch or transmucosal administration will be used alone.

Likewise, a smoking cessation program for the light smoker can be developed using the compositions and methods described herein. For example, a transdermal patch containing a relatively low loading of nicotine, typically containing nicotine in the range of about 10–30 mg, and preferably, about 20–25 mg, optionally, with the transmucosal administration of nicotine, will be used for a period of from about 4 to 8 weeks. During the final phase or weaning period, either the patch or the transmucosal formulation will be used alone.

Of course, with some individuals, administration of the transmucosal formulation may be sufficient to reduce the strong desire for cigarette smoking. Thus, and with many patients, it is possible to reduce the incidence of smoking with either the transdermal patch or the transmucosal formulation alone.

Of course, the transdermal nicotine patches and the transmucosal administration of nicotine can also be used according to a dosage pattern prescribed by a physician. The dosage pattern will vary with the indication. For example, in addition to use in smoking cessation or reduction therapy, the compositions and methods described herein can be used for the treatment of Alzheimer's Disease, ulcerative colitis and related conditions, and diseases associated with reduced central cholinergic function, loss of cholinergic neurons, significant reduction in nicotine receptor binding, neurodegenerative dementia, or cognition and memory impairment, and other diseases responsive to nicotine therapy. See Masterson (1991) U.S. Pat. No. 5,069,904; Wesnes and Warburton (1984) *Psychopharmacology* 82:147–150; and Warburton et al. (1986) *Psychopharmacology* 89:55–59.

As will be evident from the previous discussion, the ability to measure the patient's nicotine blood plasma levels can be of tremendous value in tailoring a smoking cessation or other therapy to the patient's needs. There has been very little discussion in the literature of using direct or indirect measurement of nicotine blood levels as an integral part of smoking cessation therapy. The traditional interest in quantifying nicotine blood levels has been related to research on efficacy of smoking cessation therapies. For example, research studies commonly used various measurement techniques to attempt to verify self-reports of smoking frequencies by study subjects. These include the measurement in saliva and blood plasma of nicotine, cotinine (the primary metabolite of nicotine), carboxyhemoglobin, and thiocyanate; and the measurement in expired air of carbon monoxide. The most frequently cited technique is the quantification of cotinine, a nicotine metabolite, in saliva. The quantification of cotinine in blood fluids can be accomplished by gas-liquid chromatography, radioimmunoassay, and liquid chromatography. (For a discussion of liquid chromatographic assays for cotinine, see Machacek and Jiang (1986) *Clin. Chem.* 32:979–982, herein incorporated by references.)

The present invention also comprises the direct or indirect measurement of nicotine blood levels as an integral part of methods for treating conditions responsive to nicotine therapy, and particularly for smoking cessation therapy and for reducing nicotine craving. The nicotine blood levels can be measured before, during, or after the administration of nicotine, either transdermally or transmucosally, as an aid in determining the amount of nicotine to be administered and the frequency of administration. In a preferred embodiment, saliva samples are taken from the patients and used for measurement of cotinine, as a biochemical marker of nicotine blood plasma levels. Cotinine levels are determined using any of the analytical methods known to those skilled in the art. In a particularly preferred embodiment, the cotinine assay would be portable and easily and simply accomplished by the patient, as in an assay kit or strip indicator.

The invention is now further illustrated by Examples 1 to 40, which are exemplary but nonlimiting.

EXAMPLES 1–7

Monolith Embodiments

Example 1

Monolithic patches were made as follows. A solution of nicotine-loaded adhesive was made by mixing a liquid adhesive/solvent solution (GELVA 737, Monsanto Corp.), 12.36 wt % liquid nicotine and 0.25 wt % BHT and agitating the resulting solution on a bottle roller for 12 hours. A 2 mL layer of the above solution was then coated onto the backing material (Scotchpak 1109) using a knife over roll coating head. The coated-backing was then passed through an oven at temperatures from 50°–55° C. at a speed of 5 ft/min for a total dwell time of 3 minutes. Patches with an area of 20 cm$^2$ were cut from the finished matrix with a rotary die punch.

Example 2

Monolithic patches were made by the procedure as described in Example 1, except that the amount of liquid nicotine was increased to 15.05 wt %.

Example 3

Monolithic patches were made as follows. A solution of nicotine-loaded Pellethane™ 2363-80AE was made by mixing Pellethane pellets into tetrahydrofuran, adding 10 wt % liquid nicotine, and agitating on a bottle roller for three days. A layer of backing material grade 3M-1005 was spread in a petri dish and covered with the matrix mixture. The petri dish was covered, and the matrix was left for the solvent to evaporate at room temperature. Patches with an area of 3.88 cm² were cut from the finished matrix with a punch.

Example 4

Monolithic patches were made and tested by the same procedure as described in Example 3, except that the nicotine content of the matrix mixture was 17 wt %.

Example 5

Monolithic patches were made and tested by the same procedure as described in Example 3, except that the nicotine content of the matrix mixture was 23 wt %.

Example 6

Monolithic patches were made and tested by the same procedure as described in Example 3, except that the nicotine content of the matrix mixture was 33 wt %.

Example 7

Monolithic patches were made and tested by the same procedure as described in Example 3, except that the nicotine content of the matrix mixture was 50 wt %.

Example 8

The physical characteristics for two particularly preferred nicotine transdermal patches of the present invention are shown below in Table III.

TABLE III

| Property | Low Dosage Patch | High Dosage Patch |
| --- | --- | --- |
| Dosage Strength | 22 mg/20 cm² | 27 mg/20 cm² |
| Size (cm²) | 20 | 20 |
| Nicotine content (mg) | 31.4 | 37.7 |
| 24 Hour Delivery (mg)[2] | 22 | 27 |
| Flux (mg/cm²/24 hour)[3] | 1.1 | 1.35 |
| Total Nicotine Delivered (%) | 73 | 75 |
| Patch Weight (mg) | 837 | 843 |
| Thickness (microns) | 333 | 344 |

[2]Based on residual content from in vivo performance.
[3]Estimated from in vivo performance.

The compositions of two particularly preferred nicotine patches are shown below in Table IV.

TABLE IV

| Composition | Nicotine Patch A | Nicotine Patch B |
| --- | --- | --- |
| Dosage | 22 mg/20 cm² | 27 mg/20 cm² |
| Nicotine content (mg) | 31.4 | 37.7 |
| Acrylic adhesive matrix (mg) | 70.2 | 70.2 |
| Butylated hydroxytoluene (mg) | 0.6 | 0.6 |
| Polyester film laminate (mg) | 76.0 | 76.0 |
| Acrylate skin adhesive (mg) | 358.0 | 358.0 |
| Polyester release liner (mg) | 302.4 | 302.4 |
| Total (mg) | 837.2 | 843.2 |

Example 9

Membrane Flux Tests

Promising membrane polymers that appeared to be able to withstand nicotine were tested for their nicotine permeability. The experimental procedure in each case was as follows. Samples of the films were mounted in teflon flow-through diffusion cells. Buffered isotonic saline was circulated through the bottom of the cell. Membrane samples were mounted on the bottom of each cell fixed by the threaded neck that also acts as the drug solution reservoir. The exposed area of the membrane was 3.9 cm². The membrane permeability was measured by the rate of permeation of nicotine into the saline solution. The samples were:

Dartek™ F101: nylon 6,6

Sclairfilm™ HD-2-PA: high density polyethylene

Sclairfilm™ LWS-2-PA: medium density polyethylene

Hytrel™ 5556: polyester elastomer

B410: high density polyethylene

ELVAX™ 880: ethylene/vinyl acetate copolymer, 7.5 wt % vinyl acetate

Saran™ 18L: polyvinylidene chloride

The results are summarized in Table V[4].

TABLE V

| Membrane | Thickness (μm) | Nicotine Flux (μg/cm² · hr) | Nicotine Permeability (μg · 100 μm/ cm² · hr) |
| --- | --- | --- | --- |
| Dartek ® F101 | 78 | 20 | 16 |
| Sclairfilm ® HD-2-PA | 22 | 60 | 27 |
| Sclairfilm ® LWS-2-PA | 50 | 45 | 22 |
| Hytrel ® 5556 | 250 | 10 | 25 |
| B410 | 50 | 20 | 10 |
| ELVAX ® 880 | 100–150 | >200 | >200 |
| Saran ® 18L | 50 | 16 | 8 |

[4] Test conditions: 30° C., released into saline from 3.9-cm² test devices.

Example 10–14

Reservoir Embodiments

Example 10

Experimental patches were made by heat sealing a backing of Scotch™ 1006 composite polyester tape to a 100- mu m thick film of Elvax 880. The resulting pouches were filled with approximately 200 mu L of nicotine, and the injection hole covered with a plug of hot melt glue. The finished characteristics of the patches were tested by the procedure described in Example 3, and the nicotine was released into saline at 37° C. The patches exhibited very high initial fluxes of the order 2 mg/cm²·h. Half the nicotine load was delivered within the first 15–20 hours.

Example 11

The patch-making procedure and release tests described in Example 9 were repeated using the same membrane, but with a load of 200 mu L of 20 wt % sodium sulfate solution containing a 5% suspension of nicotine. The patches exhibited a very high initial drug burst, followed by an average flux of about 8.5 mu g/cm²·h for the rest of the test period.

Example 12

Experimental patches containing a disc of microporous nylon were made. A disc having an area of 3.9 cm² was punched from a sheet of microporous nylon 6,6. The disc was glued to a nonporous 78- mu m thick film of Dartek F101. The disc was wetted with nicotine. The disc could hold about 20–25 mu L of nicotine. The membrane/disc assembly was heated sealed to a backing of Scotch 1006 or 1220 composite polyester tape. The finished patches had an effective membrane area of 3.9 cm$^2$. The release characteristics of the patches were tested by the procedure described in Example 3. The flux from these patches was about 10 mu g/cm$^2$·h during the first 10 or 15 hours, rising to about 20 mu g/cm$^2$·h after about 20–25 hours.

Example 13

The patch-making procedure and release tests described in Example 11 were repeated with a 22- mu m thick film of Sclairfilm HD-2-PA as the membrane. The flux from the patch remained roughly constant at about 80 mu g/cm$^2$·h for the first 60 hours, falling to about 30 mu g/cm$^2$·h thereafter.

Example 14

The patch-making procedure and release tests described in Example 11 were repeated with a 50- mu m thick film of Sclairfilm HD-2-PA as the membrane. The flux from the patch remained roughly constant at about 45–50 mu g/cm$^2$·h.

Examples 15–20

Mixed Monolith/Membrane Systems

Monoliths containing 50% nicotine were made by the same general procedure as described in Example 3. For Example 14, a membrane of 100- mu m thick Sclairfilm HD-2-PA was cast onto the monolith. For Example 15, a 38-mu m thick membrane of polyethylene grade HD-106 obtained from Consolidated Thermoplastics was cast onto the monolith. For Examples 16 and 17, the membranes of Examples 14 and 15 were coated with a 25- mum thick layer of BIO PSA grade X7-2920. For Example 18, the monolith was coated with polyethylene, double-sided, medical adhesive tape grade 3M-1509. For Example 19, the monolith was coated with polyethylene, double-sided, medical adhesive tape grade 3M-1512.

Release tests were carried out as with the previous examples. The upper curve shows the nicotine release from the monolith loaded with 50% nicotine without any membrane or adhesive. As can be seen, the presence of the membrane or membrane tape brings the steady-state flux down to 50 mu g/cm$^2$·h or less.

Examples 21–24

Monoliths containing 40% nicotine were made by the same general procedure as described in Example 3. For Example 20, the monolith was cast with the blade height set at 1,000 mu m. For Example 21, the monolith was cast with the blade height set at 1,500 mu m. For Example 22, the monolith was cast with the blade height set at 2,000 mu m. For Example 23, the monolith was cast with the blade height set at 2,500 mu m. All monoliths were covered with 3M-1512 medical tape. Release tests were carried out as for the previous examples. A more pronounced burst effect was observed with the thicker monoliths, containing more nicotine. The 1,500 mu m cast monolith maintained an average flux of about 500 mu g/cm$^2$·h for 24 hours, and released a total of about 4 mg/cm$^2$ in the first 5 hours. The 1,000 mu m cast monolith maintained an average flux of about 120 mu g/cm$^2$·h for 24 hours, and released a total of about 1.5 mg/cm$^2$ in the first 5 hours.

Examples 25–28

Monoliths containing varying loads of nicotine were made as follows. A solution of nicotine-loaded Pellethane 2363-80AE was made by mixing Pellethane tablets and 12 wt % nicotine into tetrahydrofuran in a sealed mixing vessel. The solution was stirred for four hours. The backing material grade 3M #1109 was then coated on a knife over roll coater, and the solvent was driven off in three successive ovens at 24° C., 35° C., and 36° C., respectively. The cast film was then laminated to 3M MSX 100/75, which is a double-sided adhesive that consists of an adhesive layer, a polyethylene membrane, a second adhesive layer, and a release liner.

For Example 24, the monolith contained 37 mg of nicotine, with a patch area of 5 cm$^2$. For Example 25, the monolith contained 74 mg of nicotine, with a patch area of 10 cm$^2$. For Example 26, the monolith contained 60 mg of nicotine, with a patch area of 20 cm$^2$. For Example 27, the monolith contained 54 mg of nicotine, with a patch area of 30 cm$^2$.

Device release rate measurements were made as follows. Each transdermal system was attached to the disk assembly, adhesive side up, of a USP Dissolution Bath, as described in The U.S. Pharmacopeia XXII, The National Formulary XVII; U.S. Pharmacopeial Convention, Inc.: Rockville, Md., 1989; pp 1578–1583, herein incorporated by reference. The disk assembly was placed inside the dissolution vessel, which contained 500 mL of degassed, deionized water maintained at a constant temperature of 32+/–0.5° C. The paddle was operated at a constant rate of 50 rpm at 25+/–2 mm from the surface of the disk assembly. Periodic samples were taken for HPLC analysis using a Dionex PCX-500 reverse-phase/ion exchange column. As shown, nicotine release per unit area is very similar for Examples 24 and 25, which have identical nicotine loadings of 7.4 mg/cm$^2$. For Examples 26 and 27, nicotine release per unit area declines as nicotine loadings of the patches decline.

Examples 29–31

Figure 5:
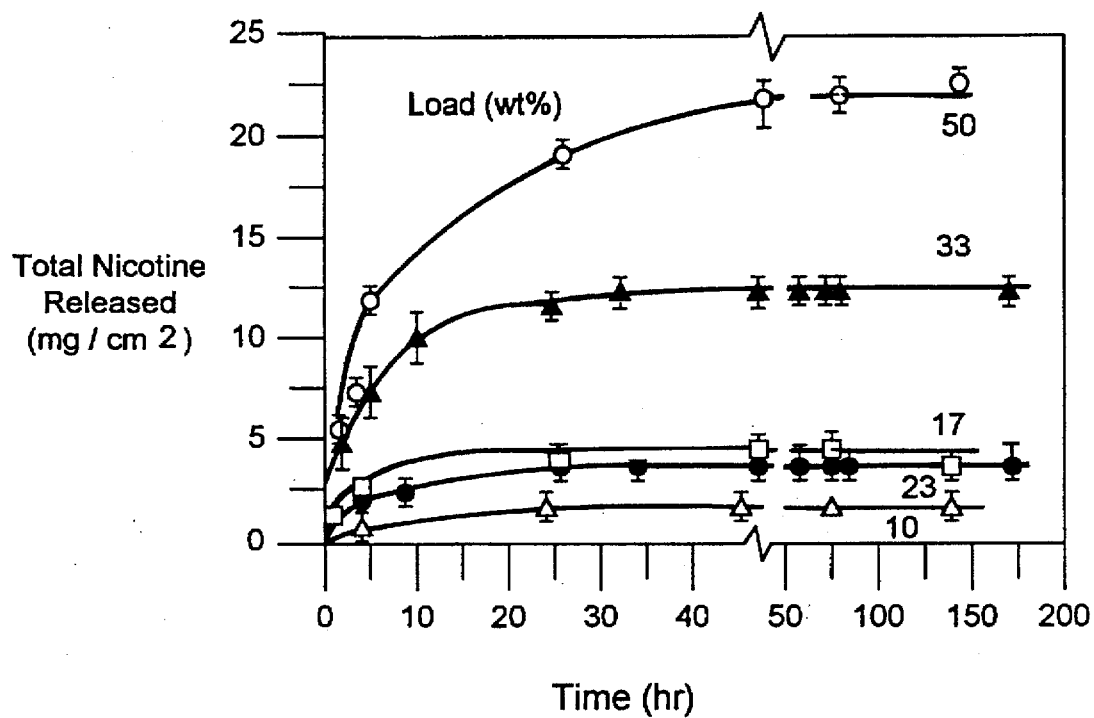
FIG. 5 is a graph of total nicotine release (milligrams (mg)/square centimeter (cm$^2$)) against time (hours (hr)) for a polyurethane/nicotine monolith.
Figure 6:
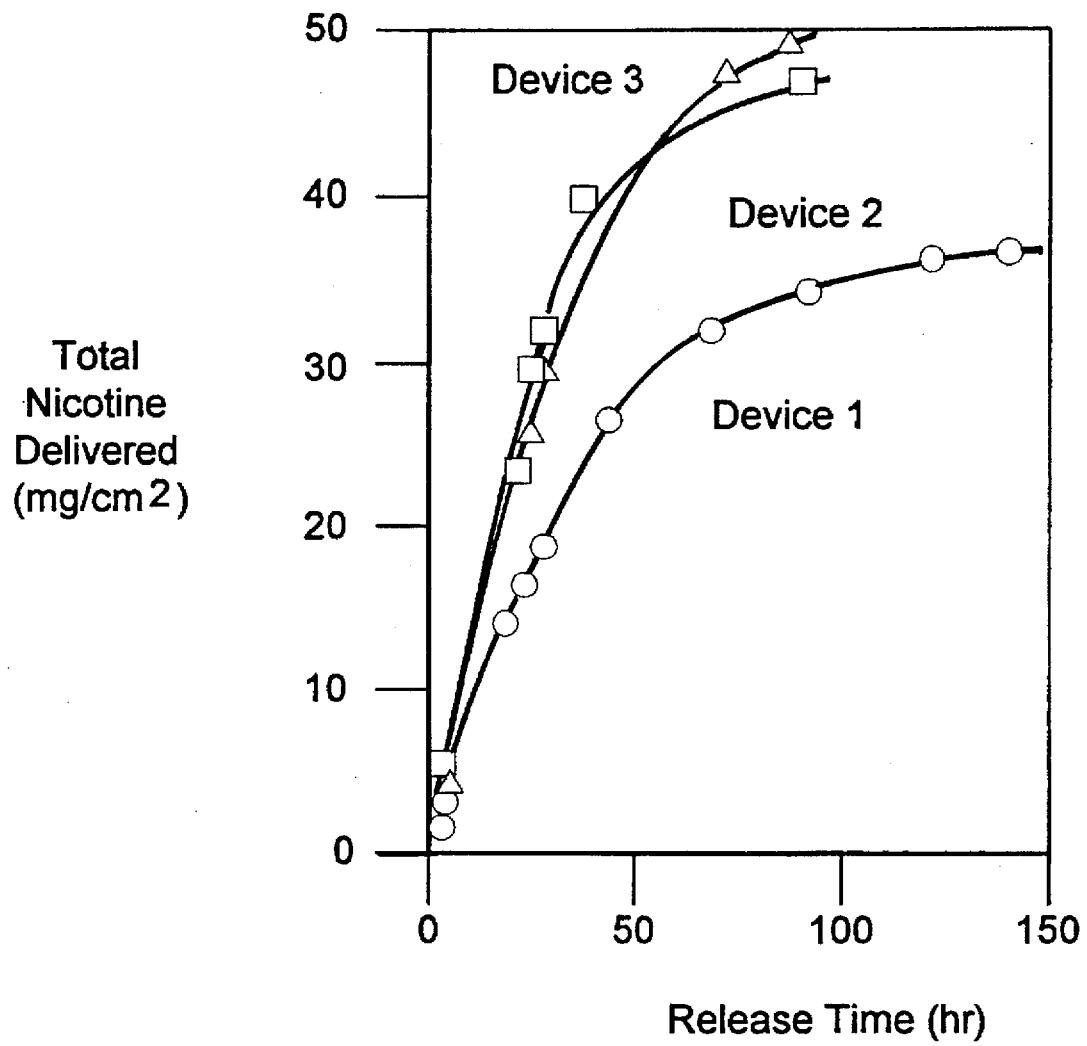
FIG. 6 is a graph of nicotine delivery (mg/cm$^2$) through 100-micron thick Elvax 880 membranes, from a patch containing 200 mu L pure nicotine, with a membrane area of 4.5 cm$^2$, as a function of time (hr).
Figure 7:
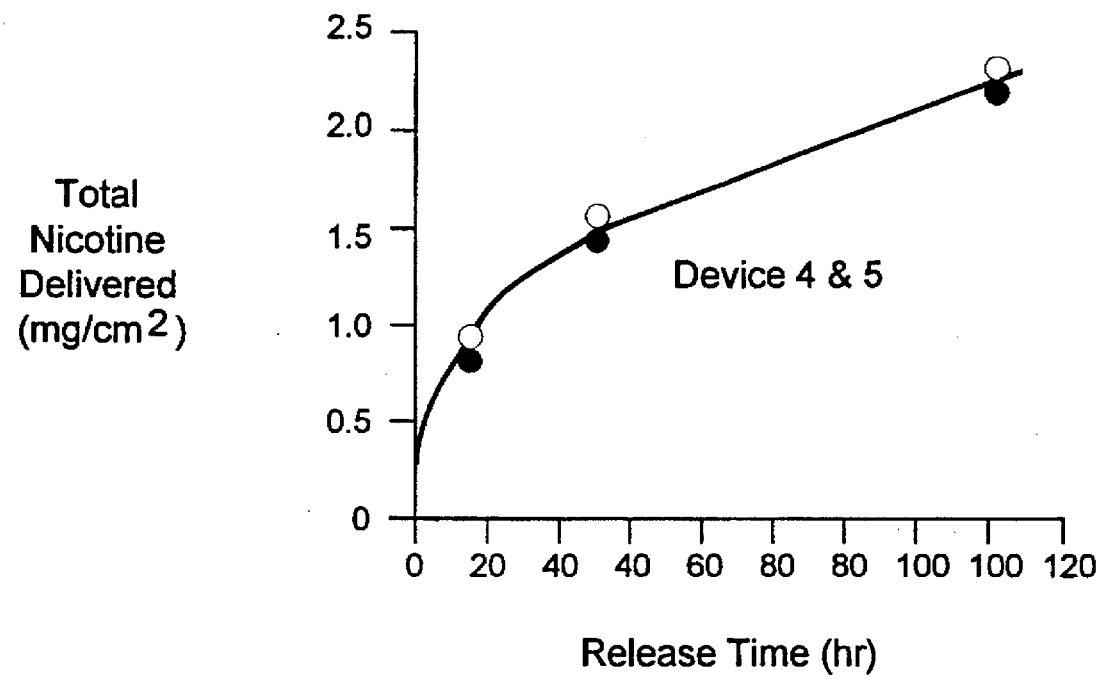
FIG. 7 is a graph of nicotine delivery (mg/cm$^2$) through 100-micron thick Elvax 88 membranes, from a patch containing 200 mu L of a 5% suspension of nicotine in a 20 wt % sodium sulfate solution, with a membrane area of 4.5 cm$^2$, as a function of time (hr).
Figure 8:
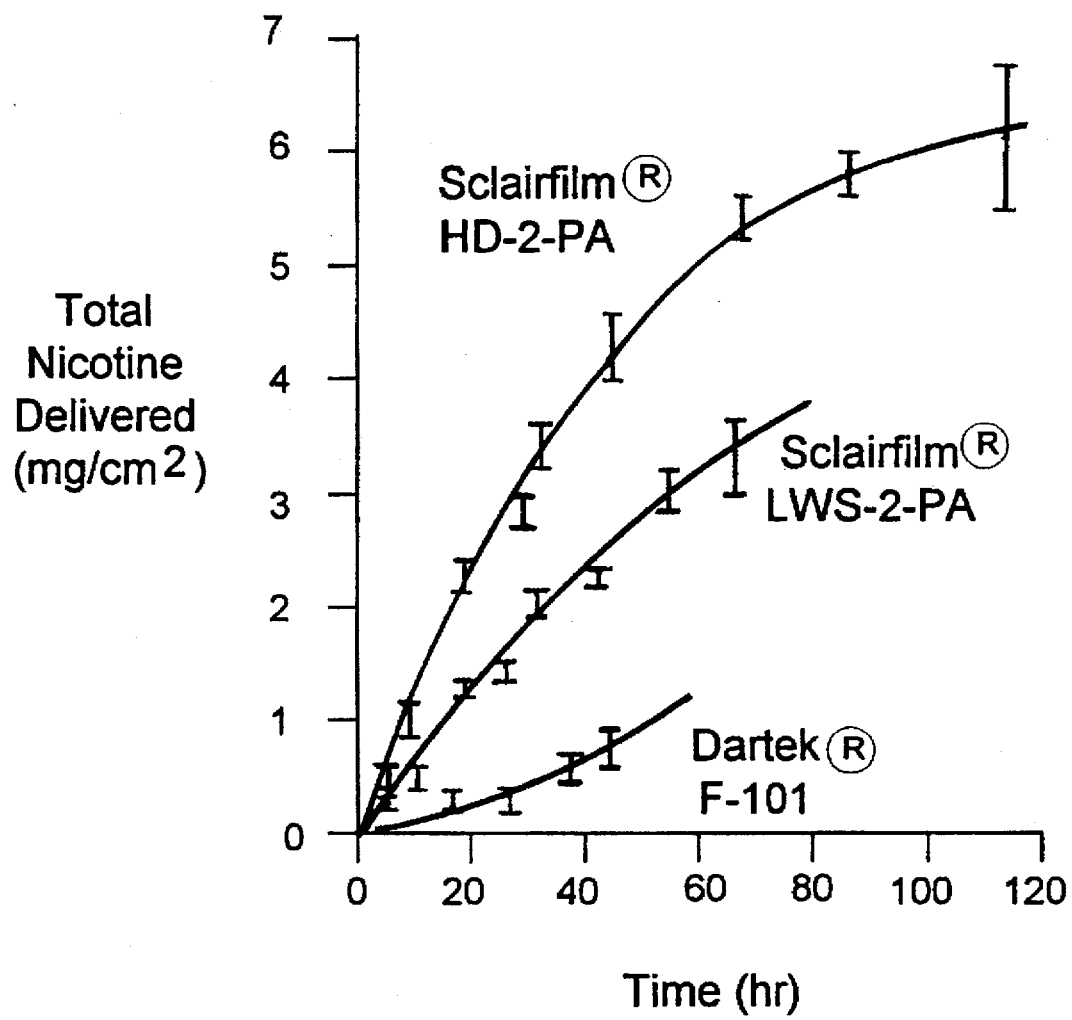
FIG. 8 is a graph of nicotine delivery (mg/cm$^2$) from patches with nylon or polyethylene membranes, as a function of time (hr). The nicotine content is 20–25 mg, and the patch area is 3.9 cm$^2$.
Figure 9:
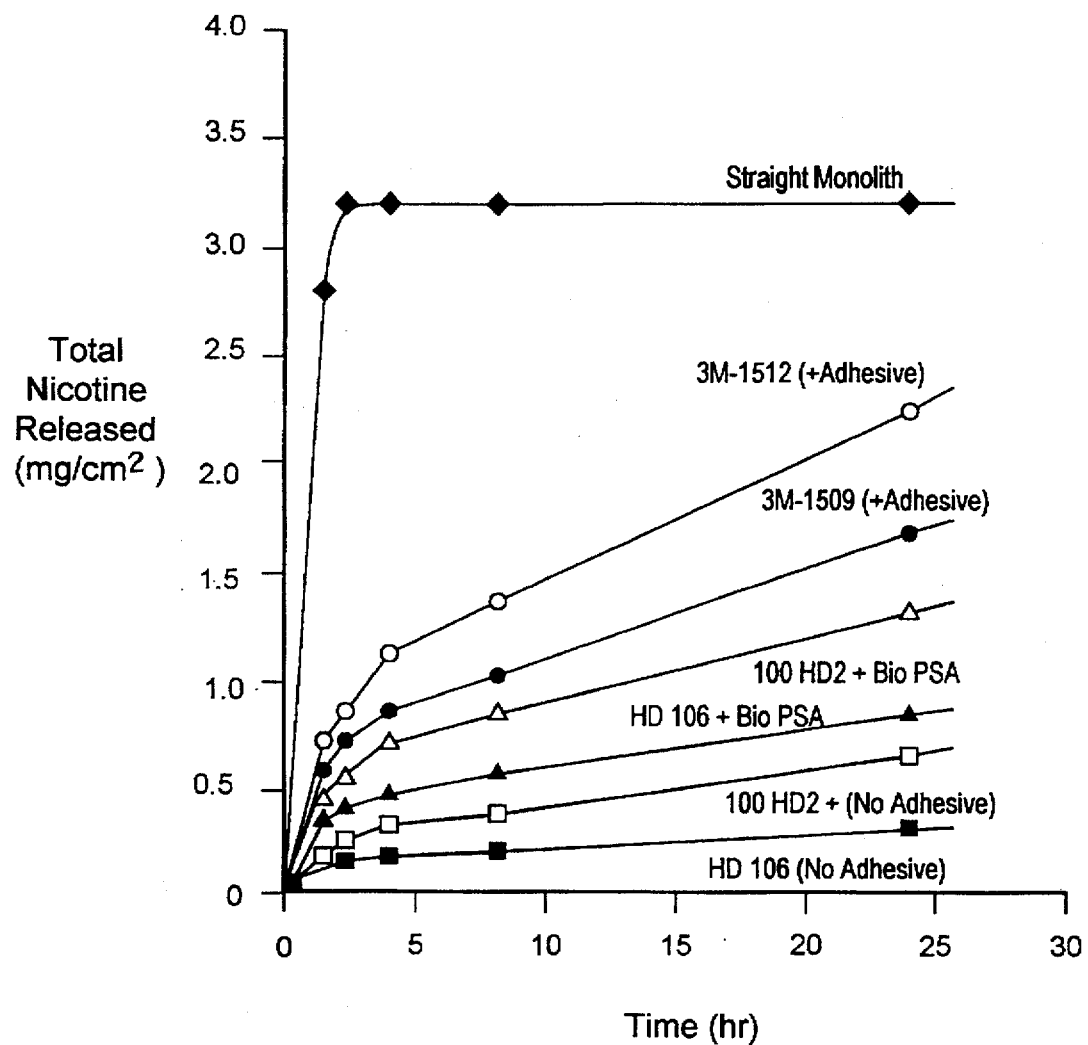
FIG. 9 is a graph of nicotine delivery (mg/cm$^2$) from mixed monolith/membrane patches containing a 50% nicotine load, using a polyethylene membrane or a polyethylene medical tape, as a function of time (hr).
Figure 10:
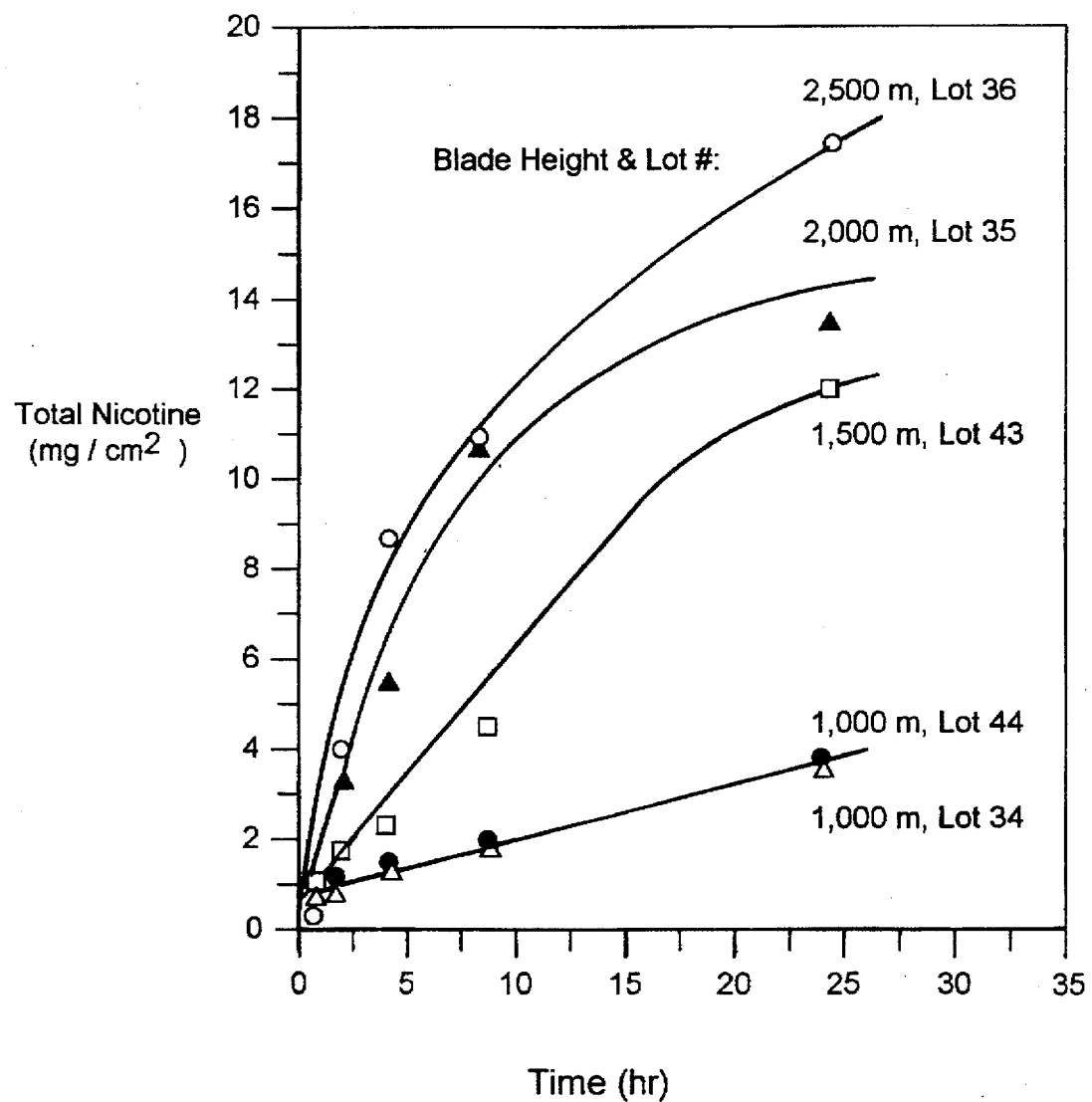
FIG. 10 is a graph of nicotine delivery (mg/cm$^2$) from mixed monolith/membrane patches containing a 40% nicotine load, using a polyethylene membrane or a polyethylene medical tape, as a function to time (hr).
Figure 11:
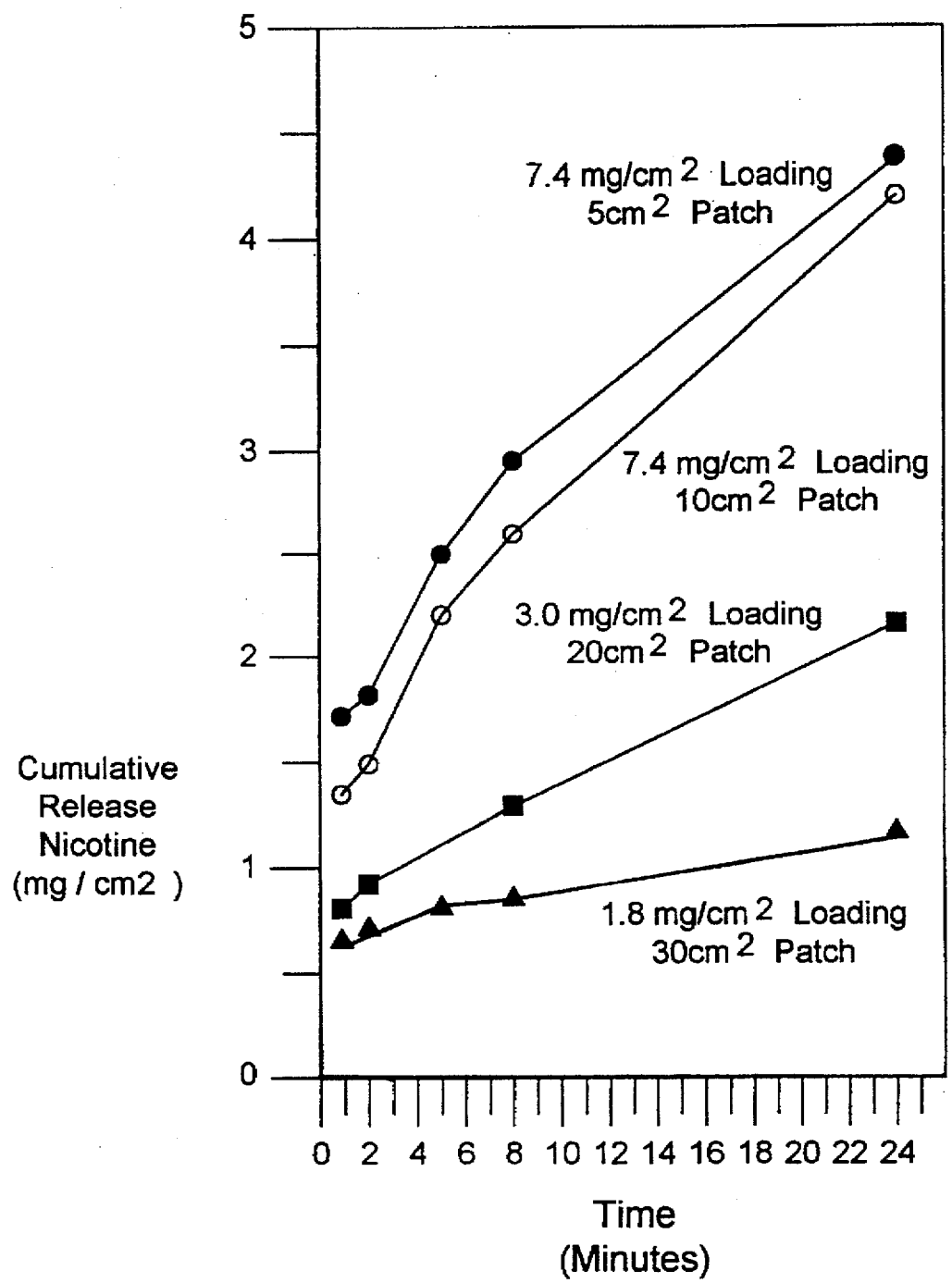
FIG. 11 is a graph of nicotine delivery (mg/cm$^2$) from mixed monolith/membrane patches of various nicotine loads and sizes, using a double-sided adhesive that contains a polyethylene membrane, as a function of time (min).
Figure 12:
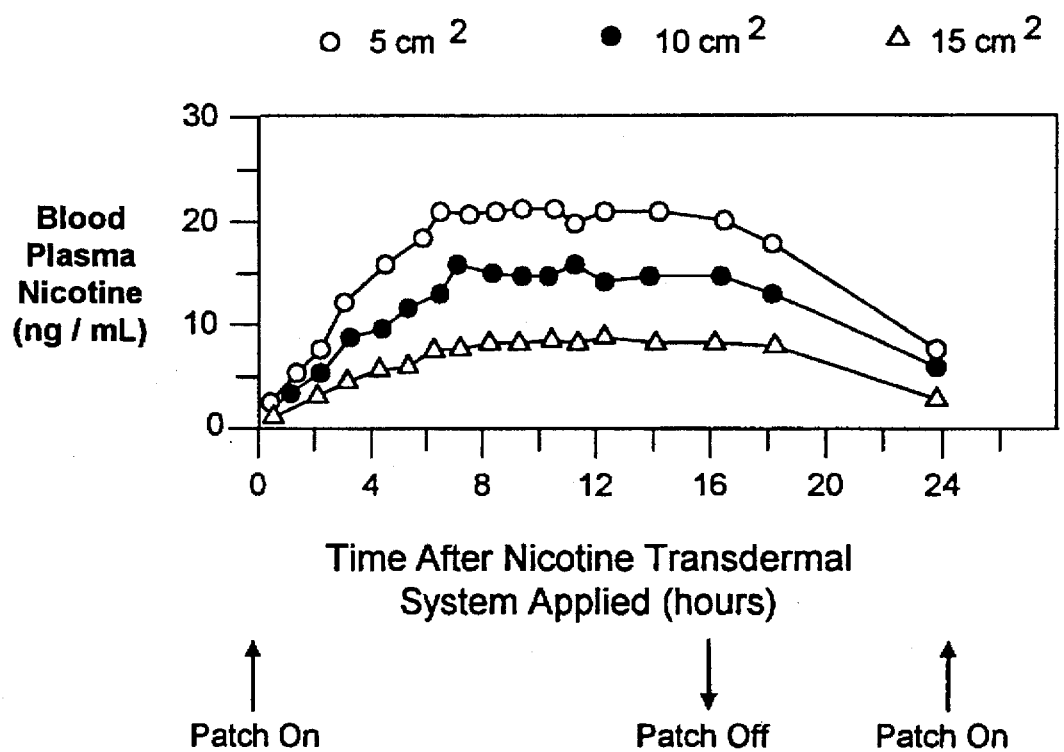
FIG. 12 is a graph of nicotine plasma levels (ng/mL) after application of a transdermal nicotine systems with varying application areas, as a function of time (hr).

The blood levels shown in FIG. 5 were obtained from 6 adult male smokers who had already developed a strong tolerance to nicotine. For all examples, transdermal nicotine systems used were manufactured as described in Examples 24–27, and each contained a total of 37 mg nicotine in a patch with an area of 5 cm$^2$, as in Example 24. For Example 28, a single 5 cm$^2$ transdermal nicotine patch was applied to the right forearm of each subject, and the patch remained affixed to the forearm for 16 hours. The lowest curve presents the average nicotine plasma level obtained. For Example 29, two 5 cm$^2$ transdermal nicotine patches were applied to the right forearm of each subject, and the patches remained affixed to the forearm for 16 hours. The middle curve presents the average nicotine plasma levels obtained. For Example 30, three 5 cm$^2$ transdermal nicotine patches were applied to the right forearm of each subject, and the patches remained affixed for 16 hours. The top curve presents the average nicotine plasma levels obtained. These test subjects were able to tolerate as many as three 5 cm$^2$ patches with a total in vitro delivery of almost 70 mg/24 h without any untoward symptoms.

Example 32

In Vivo Studies

In vivo studies have been conducted to establish the bioavailability of nicotine from the transdermal patches of the present invention. The study, employing 12 healthy male smokers, consisted of three treatment periods which were run in a balanced crossover design to compare the steady state pharmacokinetics of the 22 and 27 mg patches of the present invention with the PROSTEP 22 mg transdermal nicotine patch, available from elan pharma, Ltd., Athlone, County Westmeath, Ireland, and manufactured by Lederle Laboratories Division, American Cyanamid Company, Pearl River, N.Y.

Figure 14:
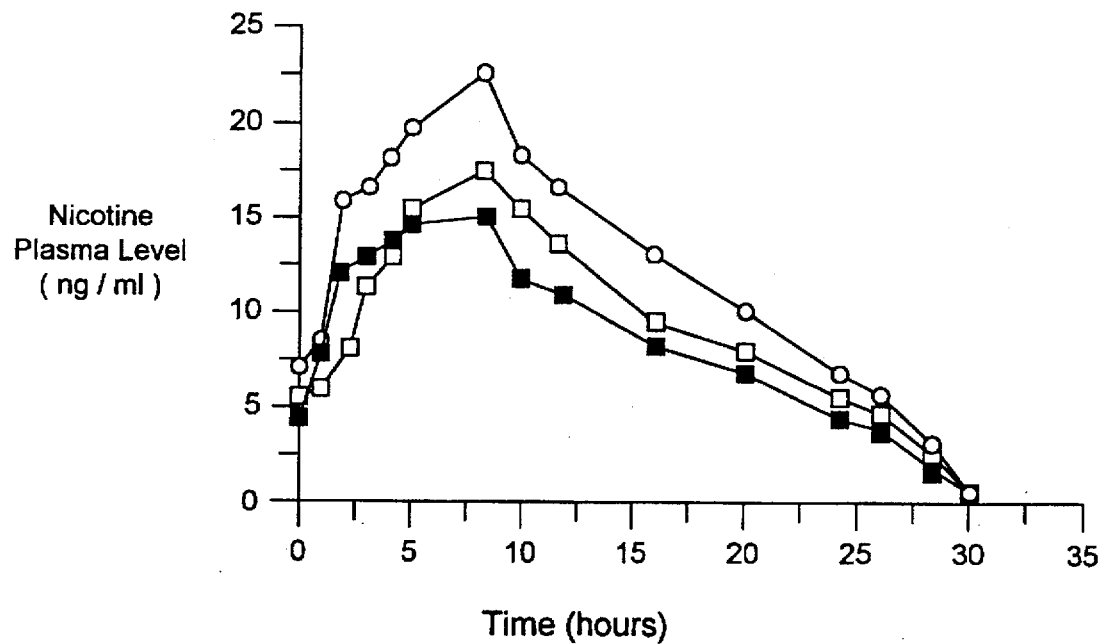
FIG. 14 is a graph of blood plasma levels (ng/mL) after application of the transdermal nicotine systems of the present invention delivering either 22 mg (□) or 27 mg (○) of nicotine or the PROSTEP 22 mg (■) patch as a function of time (hr).

After a 60 hour run-in phase, the nicotine patches were worn for a 24 hour period for each of the five consecutive days of the treatment period. The resulting blood plasma levels, along with those of the PROSTEP 22 mg patch are shown in FIG. 14. The patches of the present invention were well tolerated.

The steady-state parameters for currently marketed nicotine transdermal systems are summarized in Table VI below.

TABLE VI

| Transdermal Patch[5] | Cmax[6] (ng/mL) | Cavg[7] (ng/mL) | Cmin[8] (ng/mL) | Tmax[9] (hrs) |
|---|---|---|---|---|
| Habitrol ™ (21 mg/day)[10] | 17 ± 2 | 13 ± 2 | 9 ± 2 | 6 ± 3 |
| PROSTEP ™ (22 mg/day) | 16 ± 6 | 11 ± 3 | 5 ± 1 | 9 ± 5 |
| NICODERM SM (21 mg/day) | 23 ± 5 | 17 ± 4 | 11 ± 3 | 4 ± 3 |
| NICOTROL SM (15 mg/day) | 13.0 ± 3.1 | 8.7 ± 2.1 | 2.5 ± 0.8 | 8 ± 3 |
| PATCH OF EXAMPLE 1 (22 mg/day) | 16.1 ± 7.1 | 11.2 ± 4.1 | 4.8 ± 1.8 | 8.4 ± 1.8 |
| PATCH OF EXAMPLE 2 (27 mg/day) | 23.4 ± 8.1 | 14.5 ± 3.3 | 5.7 ± 1.9 | 8.4 ± 3.3 |

[5]Competitor product data taken from product inserts.
[6]Cmax = maximum observed plasma concentration.
[7]Cavg = average plasma concentration
[8]Cmin = minimum observed plasma concentration
[9]Tmax = time of maximum plasma concentration
[10]Available from BASEL Pharmaceuticals, a division of CIBA-GEIGY Corporation, Summit, NJ.

Example 32

Buffered Nicotine Sublingual Tablet

FORMULATION

| Ingredient | mg/tablet |
|---|---|
| Nicotine free base | 2.0 |
| Microcrystalline cellulose[11] | 50.0 |
| Magnesium stearate | 2.6 |
| Colloidal silica[12] | 5.0 |
| Gum arabic | 4.0 |
| Polyvinyl alcohol | 1.2 |
| Starch | 53.0 |
| Mannitol | 32.0 |
| Lactose | 38.4 |
| Sucrose | 137.0 |
| Disodium hydrogen phosphate | 9.7 |
| Citric acid | 0.3 |
| Mint flavor[13] | 4.0 |
| Ammonium glycyrrhizinate[14] | 4.0 |

[11]Avicel PH 101 ™
[12]Aerosil 200 ™
[13]*Pulvaromas* mint
[14]Glycamil ™

Manufacturing Method-Granulation

1. Avicel PH 101 and Aerosil 200 are well mixed in a Turbula mixer for at least 10 min.

2. Nicotine is adsorbed onto the blend obtained in Step 1., which acts as a carrier. This is accomplished by very carefully mixing nicotine in a mortar with half the quantity of the blend. When a good dispersion is obtained, the remaining quantity is added and mixed well until a homogeneous dispersion is achieved.

3. A granulate is then prepared by mixing in a Tonazzi kneading machine gum arabic, polyvinyl alcohol, mannitol, starch, disodium hydrogen phosphate, citric acid, lactose, and sucrose. Water is used as a granulating liquid.

4. The mixture obtained is then granulated using an Alexanderwerk granulator equipped with a No. 2 screen.

5. The granulate is dried in a Buhler oven with circulating air at 50° C. up to a moisture content of 3%.

6. using a Turbula mixer, the dispersion of nicotine onto Avicel PH 101 and Aerosil 200 is mixed with the granulate obtained in Step 5. for at least 15 min.

7. Magnesium stearate, Pulvaromas mint, and Glycamil are added in the Turbula mixer and mixed with the blend obtained in Step 6. for at least 15 min.

8. The blend of powders is compressed using single punch tablet press equipped with a 9 mm diameter biconvex punch, obtaining tablets with a weight of 343.2 mg and hardness of 15 Kp.

Example 33

Buffered Nicotine Sublingual Capsule (Chewable Soft Gelatin Capsules)

FORMULATION

| Ingredient | mg/tablet |
|---|---|
| Nicotine free base | 2.0 |
| Glycerol | 20.40 |
| Water | 34.00 |
| Sodium saccharinate | 0.50 |
| Polyethylene glycol[15] | 386.00 |
| Mint flavor[16] | 0.70 |
| Ammonium glycyrrhizinate[17] | 0.70 |
| Disodium hydrogen phosphate | 12.90 |
| Citric acid | 0.40 |

[15]Carbowax 400 ™
[16]*Pulvaromas* mint
[17]Glycamil

Procedure

1. Glycerol, water, sodium saccharinate, and Carbowax 400 are mixed in a stainless steel reactor for at least 15 min.

2. Disodium hydrogen phosphate and citric acid are added and mixed for at least 10 min.

3. While stirring well, nicotine, Pulvaromas, and glycamil are added. The mixture is stirred for at least 15 min.

4. The mixture obtained in Step 2. is transferred to a stainless steel container.

5. The following shell constituents are introduced into a stainless steel container: gelatin, glycerin, titanium dioxide, sodium ethyl hydroxybenzoate, and sodium propyl hydroxybenzoate. (For a capsule content of 450 mg, typical quantities of shell constituents would be gelatin-140 mg, glycerin-67 mg, titanium dioxide-2.8 mg, sodium ethyl hydroxybenzoate-0.6 mg, and sodium propyl hydroxybenzoate-0.5 mg.) They are melted at 70° C. The mixture is stirred for 15 min. to make it homogeneous.

6. The Pulvaromas mint is added to the melted mixture for the shell and stirred for 2 min.

7. The Scherer capsulation machine is filled with the melted mixture obtained in Step 6.

8. The capsules are produced in the predetermined shape and volume, and the solution obtained in Step 3. is injected inside them by means of special nozzles.

Example 34

Nicotine Lozenge

FORMULATION

| Ingredients | mg/tablet |
| --- | --- |
| Nicotine | 1.0 |
| Mannitol | 200.0 |
| Xylitol | 1309.0 |
| Mint flavor | 20.0 |
| Ammonium glycyrrhizinate | 15.0 |
| Sodium carbonate | 5.0 |
| Sodium bicarbonate | 15.0 |
| Hydrogenated vegetable oil | 25.0 |
| Magnesium stearate | 10.0 |

Procedure

1. Nicotine was dispersed in mannitol.
2. The powders were mixed.
3. The mixture was compressed with a suitable alternative tablet press, using a square 16 mm-punch dosing 1600 mg/tablet.
4. Tablets were packed into strips of aluminum/Barex.

Example 35

FORMULATION

| Ingredients | mg/tablet |
| --- | --- |
| Nicotine | 1.0 |
| Mannitol | 200.0 |
| Xylitol | 1316.5 |
| Tobacco flavor | 6.0 |
| Colloidal silica | 1.5 |
| Ammonium glycyrrhizinate | 15.0 |
| Sodium carbonate | 5.0 |
| Sodium bicarbonate | 15.0 |
| Hydrogenated vegetable oil | 30.0 |
| Magnesium stearate | 10.0 |

Procedure

1. Nicotine was dispersed in mannitol.
2. The powders were mixed.
3. The mixture was compressed with a suitable alternative tablet press, using a square 16 mm-punch dosing 1600 mg/tablet.
4. Tablets were packed into strips of aluminum/Barex.

Example 36

Nicotine Lozenge

FORMULATION

| Ingredients | mg/tablet |
| --- | --- |
| Nicotine | 1.0 |
| β-cyclodextrin | 109.0 |
| Water | 10.0 |
| Xylitol | 1400.0 |

FORMULATION -continued

| Ingredients | mg/tablet |
| --- | --- |
| Mint flavor | 20.0 |
| Ammonium glycyrrhizinate | 15.0 |
| Sodium carbonate | 5.0 |
| Sodium bicarbonate | 15.0 |
| Hydrogenated vegetable oil | 25.0 |
| Magnesium stearate | 10.0 |

Procedure

1. Nicotine was dispersed in β-cyclodextrin.
2. The powders were mixed.
3. The mixture was compressed with a suitable alternative tablet press, using a square 16 mm-punch dosing 1600 mg/tablet.
4. Tablets were packed into strips of aluminum/Barex.

Example 37

Manufacturing Process for Nicotine Lozenge Formulation with Xylitol, Mannitol, and Mint Flavor 1. Preparation of the nicotine-mannitol mixture One kg of mannitol was sieved through a 50 mesh sieve and was placed in a Tonazzi mixer. Next, 10 g of nicotine were added slowly with mixing for 10 minutes. The mixture was transferred to a 2 liter amber glass bottle and mixed for 15 minutes in a Turbula mixer.

2. Preparation of the granulate

A quantity of 50.5 g of the mixture from (1) above and 54.5 g of Xilitab 200 (xylitol) were sieved with a 20 mesh sieve, and then were mixed with 50 g mannitol, 5 g magnesium stearate, 12.5 mg Lubritab (hydrogenated vegetable oil), 10 g mint flavor, 7.5 g ammonium glycyrrhizinate, 7.5 g sodium bicarbonate, and 2.5 g sodium carbonate, and was sieved through a 50 mesh sieve. The mixture was transferred to a 2 liter amber glass bottle and mixed for 15 minutes in a Turbula mixer.

3. Tablet formation

The mixture was tabletted in a Belloni alternative press, using a 16-mm$^2$ punch. Tablet weight was 1600 mg/tablet.

4. Packaging

The tablets were packaged into strips of paper/aluminum/Barex.

Example 38

Manufacturing Process for Nicotine Lozenge Formulation with Xylitol, β-Cyclodextrin, and Mint Flavor 1. Preparation of the nicotine—β-cyclodextrin complex An initial quantity of 56.76 g of β-cyclodextrin was placed in a 400 mL beaker and 5.68 g of $H_2O$ (equivalent to 10% of the powder) was added with stirring. The water was added in amounts of 1.9 g at a time, with stirring for 10 minutes at each step. The powder, before addition of nicotine, was similar to a wet granulate.

Next, 6.37 g of nicotine was added very slowly with stirring, and at the end of the process the granulate was stirred for 15 minutes. The obtained granulate was dried in an oven at 35° C. for 2 hours.

A sample was then analyzed for nicotine content.

2. Preparation of the dry granulate

A quantity of 5.25 g of the nicotine—β-cyclodextrin complex, 50 g of β-cyclodextrin, 5 g magnesium stearate, 12.5 g Lubritab® (hydrogenated vegetable oil), 10 g mint flavor, 7.5 g ammonium glycyrrhizinate, 7.5 g sodium bicarbonate, and 2.5 g sodium carbonate were sieved through an 80 mesh sieve.

Next, 700 g of Xilitab® 100 (xylitol) was sieved through a 50 mesh sieve.

The mixture was mixed in a Turbula mixer for 20 minutes.

3. Tablet formation

The mixture from (2) above was tabletted with a Belloni tablet press equipped with square punches. Tablet weight was 1600 mg/tablet.

4. Packaging

The tablets were put in strips of paper/aluminum/Barex having the following composition: paper 50 g/m$^2$, aluminum 12 µ thickness, 32 g/m$^2$, Barex 35 g/m$^2$.

Example 39

Nicotine Lozenge Stability Assay

One nicotine lozenge was crushed and placed in a 50 mL volumetric flask. To the flask was then added tetrahydrofuran (25 mL) and the flask was transferred to a sonicating bath where it was allowed to stand for 20 minutes. Sufficient ethyl acetate was added to bring the volume of solution up to 50 mL. A portion of this solution (1 mL) was removed and placed in a 25 mL volumetric flask. To this flask was then added a few milliliters of water and 0.25 mL of an internal standard solution consisting of 50 mg acetanilide diluted to 100 mL with water. The organic solvents were removed using a gentle nitrogen gas flow which resulted in a cloudy solution. Sufficient water was then added to the cloudy solution to bring the volume of the solution to 25 mL. The solution was then filtered through a 0.22 mcm membrane.

The amount of nicotine in the sample was determined using high performance liquid chromatography (column temperature, 30±1° C.; mobile phase, water:methanol:acetate buffer (0.1M, pH=4.0):acetonitrile 60:31:7:2, adjusted to pH=6.82 with triethylamine, filtered, and deaerated; mobil phase flow rate, 1.0 mL/min; solid phase, Supelcosil LC1808 (5 mcm) 25 centimeters (cm)×4.6 millimeters (mm), available from Supelco Inc.; and analytical wavelength 254±1 nanometers (nm)). Under these conditions, nicotine and acetanilide had retention times of about 7.7 and 9.3 minutes, respectively. The ratio of the components in the mobile phase can be varied to provide suitable elution times for the nicotine and the internal standard.

Example 40

In Vivo Measurement of Nicotine Release from a Lozenge

A clinical trial of the lozenge described in Example 32 involves six patients who are each given one lozenge on study day 1 at 8:00 a.m. A pre-dose blood sample is taken before each administration. The patients are asked to suck the lozenge. Blood samples are taken at 2.5, 5, 7.5, 10, 15, 20, 25, 30, 45, 60, 75, 90, 105, 120, and 240 minutes. In addition, immediately after the lozenge has dissolved, the patient notifies the medical staff so that the time of dissolution can be recorded.

Blood samples of 5 mL are collected in lithium heparinate tubes. Immediately after collection, the samples are cooled and centrifuged at 4° C. at 1500 rpm for 15 minutes. The plasma is then transferred to polypropylene tubes and stored at −30° C. until analysis for nicotine and cotinine. A capillary gas chromatographic method is used for the analysis of nicotine and cotinine. The detection limit is 0.8 ng/mL for nicotine and 5.0 ng/mL for cotinine. The quantitative determination limit is 1.0 ng/mL for nicotine and 10 ng/mL for cotinine.

The disclosures in this application of all articles and references, including patent documents, are incorporated herein by reference.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A method for treating a condition responsive to nicotine therapy, comprising the steps of:
   i) a first treatment with nicotine by transdermal administration to obtain nicotine blood levels of between 5 to 35 ng/mL for at least 12 hours; and
   ii) a second treatment with nicotine by transmucosal administration through the nasal membranes by the administration of an aerosol formulation to obtain maximum nicotine blood levels from 2 to 20 minutes after the transmucosal administration; and wherein the transmucosa administration provides transient blood levels of nicotine about 5 ng/mL above that provided by the transderma administration of nicotine.

2. The method as described in claim 1, wherein the transmucosal administration through the nasal membranes is obtained by the administration of an aerosol formulation in the form of a nasal spray and results in maximum nicotine blood levels from 2 to 10 minutes after the transmucosal administration of nicotine.

3. The method of claim 2, wherein the range of concentration of the nicotine in the nasal spray is generally within the range of 0.1–100 mg/mL.

4. The method of claim 2, whereto the range of concentration of the nicotine in the nasal spray is generally within the range of 1–10 mg/mL.

5. A combination of a system for transdermal administration of nicotine and a system for transmucosal administration of nicotine for use, wherein:
   a) the system for transdermal administration comprises:
      i) a nicotine depot layer, having a skin-facing side and a skin-distal side, the depot layer containing a sufficient quantity of nicotine to maintain a useful flux of nicotine from the patch for a total time period of 12 hours or more;
      ii) an occlusive backing layer in contact with and covering the depot layer on the skin-distal side; and
      iii) rate-controlling means for controlling diffusion of nicotine from the skin-facing side at a first flux of greater than zero but less than 2 mg/cm$^2$ in any hour for a first time period of greater than zero but less than 5 hours, then at a second flux between 20 and 800 mu g/cm$^2$ h for a second time period of 7 hours or more, wherein the transdermal system results in nicotine blood levels of between 5 to 30 ng/mL for at least 12 hours; and b) the system for transmucosal administration of nicotine is through the nasal membranes and is obtained by the administration of a nasal spray which provides transient blood levels of nicotine about 5 ng/mL above that provided by the transdermal administration of nicotine when the transdermal and transmucosal administration of nicotine is concurrent.

* * * * *